US008216575B2

(12) United States Patent
Yu

(10) Patent No.: US 8,216,575 B2
(45) Date of Patent: Jul. 10, 2012

(54) INHIBITION OF NEOVASCULARIZATION WITH A SOLUBLE CHIMERIC PROTEIN COMPRISING VEGF FLT-1 AND KDR DOMAINS

(75) Inventor: Michael Dechao Yu, Chengdu (CN)

(73) Assignee: Chengdu Kanghong Biotechnologies Co., Ltd., Sichuan (CN)

( * ) Notice: Subject to any disclaimer, the term of this patent is extended or adjusted under 35 U.S.C. 154(b) by 111 days.

(21) Appl. No.: 12/457,478

(22) Filed: Jun. 11, 2009

(65) Prior Publication Data

US 2010/0272719 A1    Oct. 28, 2010

Related U.S. Application Data

(63) Continuation-in-part of application No. 12/241,017, filed on Sep. 29, 2008, which is a continuation of application No. PCT/CN2007/001021, filed on Mar. 29, 2007.

(30) Foreign Application Priority Data

Mar. 31, 2006 (CN) .......................... 2006 1 0066257

(51) Int. Cl.
*A61K 38/18* (2006.01)
*C07K 14/71* (2006.01)
*C12N 15/62* (2006.01)

(52) U.S. Cl. ................... 424/134.1; 424/192.1; 514/1.1; 514/7.6; 514/13.3; 530/350

(58) Field of Classification Search ........................ None
See application file for complete search history.

(56) References Cited

U.S. PATENT DOCUMENTS

| 7,070,959 | B1 | 7/2006 | Papadopoulos et al. |
| 7,087,411 | B2 | 8/2006 | Daly et al. |
| 7,279,159 | B2 | 10/2007 | Daly et al. |
| 2008/0206238 | A1 | 8/2008 | Liu |
| 2009/0062200 | A1 | 3/2009 | Daly et al. |
| 2009/0081217 | A1 | 3/2009 | Papadopoulos et al. |

FOREIGN PATENT DOCUMENTS

WO    00/75319 A1    12/2000

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
De Vries, C., et al., "The fms-Like Tyrosine Kinase, a Receptor for Vascular Endothelial Growth Factor", Science, vol. 255, pp. 989-991, (1992).

Terman, B.I., et al., "Identification of a new endothelial cell growth factor receptor tyrosine kinase", Oncogene, vol. 6, pp. 1677-1683, (1991).
Terman, B.I., et al., "Identification of the KDR Tyrosine Kinase as a Receptor for Vascular Endothelial Cell Growth Factor", Biochemical and Biophysical Research Communications, vol. 187, No. 3, pp. 1579-1586, (1992), Academic Press, Inc.
Asano, M., et al., "An Anti-Human VEGF Monoclonal Antibody, MV833, That Exhibits Potent Anti-Tumor Activity in Vivo", Hybridoma, vol. 17, No. 2, pp. 185-190, (1998), Mary Ann Liebert, Inc.
Prewett, M., et al., "Antivascular Endothelial Growth Factor Receptor (Fetal Liver Kinase 1) Monoclonal Antibody Inhibits Tumor Angiogenesis and Growth of Several Mouse and Human Tumors", Cancer Research, vol. 59, pp. 5209-5218, (1999).
Holash, J., et al., "VEGF-Trap: A VEGF blocker with potent antitumor effects", PNAS, vol. 99, No. 17, pp. 11393-11398, (2002).
Cunningham, S.A., et al., "Identification of the Extracellular Domains of Flt-1 That Mediate Ligand Interactions", Biochemical and Biophysical Research Communications, vol. 231, pp. 596-599, Article No. RC976156, (1997), Academic Press.
Ma, Li, et al., "Identification of the ligand-binding domain of human vascular-endothelial-growth-factor receptor Flt-1", Biotechnol. Appl. Biochem., vol. 34, pp. 199-204, (2001), Portland Press Ltd, Great Britain.
Fu, X., et al., "Basic Fibroblast Growth Factor (bFGF) and Wound Healing: A multi-centers and controlled clinical trial in 1024 cases", pp. 209-211, (1998). English Abstract.
Kaplan, J.B., et al., "Characterization of a soluble vascular endothelial growth factor receptor-immunoglobulin chimera", Growth Factors, vol. 14, No. 4, pp. 243-256, (1997).
Alam, A., et al., "Heterodimerization with vascular endothelial growth factor receptor-2 (VEGFR-2) is necessary for VEGFR-3 activity", Biochemical and Biophysical Research Communications, vol. 324, pp. 909-915, (2004), Elsevier Inc.
Koh, A.H.C., et al., "Age-related Macular Degeneration: What's New", Ann Acad Med Singapore, vol. 31, pp. 399-404, (2002).
Evans, J.R., "Risk Factors for Age-related Macular Degeneration", Progress in Retinal and Eye Research, vol. 20, No. 2, pp. 227-253, (2001), Elsevier Science Ltd., Great Britain.
Hawkins, B.S., et al., "Epidemiology of age-related macular degeneration", Molecular Vision, vol. 5, pp. 26-29, (1999).
Vingerling, J.R., et al., "Epidemiology of Age-related Maculopathy", Epidemiologic Reviews, vol. 17, No. 2, pp. 347-360, (1995), The Johns Hopkins University School of Hygiene and Public Health, U.S.A.
Vinding, T., "Macula—the Eye in the Eye", Acta Ophthalmologica, vol. 73, pp. 3-32, (1995).
Rosenfeld, P.J., et al., "Ranibizumab for Neovascular Age-Related Macular Degeneration", N Engl J Med, vol. 355, No. 14, pp. 1419-1431, (2006), Massachusetts Medical Society.

(Continued)

*Primary Examiner* — Christine J Saoud
*Assistant Examiner* — Jon M Lockard
(74) *Attorney, Agent, or Firm* — Nath, Goldberg & Meyer; Joshua B. Goldberg; Tanya E. Harkins

(57) ABSTRACT

Described herein are novel soluble chimeric fusion proteins comprising amino acid sequences derived from the vascular endothelial growth factor (VEGF) receptors flt-1 and KDR, including domain 4 of KDR. The claimed chimeric fusion proteins antagonize the endothelial cell proliferative and angiogenic activity of VEGF and are useful in the treatment of neovascularization-related disease.

18 Claims, 12 Drawing Sheets

OTHER PUBLICATIONS

Brown, D.M., et al., "Ranibizumab versus Verteporfin for Neovascular Age-Related Macular Degeneration", N. Engl J Med, vol. 355, No. 14, pp. 1432-1444, (2006), Massachusetts Medical Society.

Gottlieb, J.L., "Age-Related Macular Degeneration", JAMA, vol. 288, No. 18, pp. 2233-2237, (2002), American Medical Association.

Moroney, J.W., et al., "Aflibercept in epithelial ovarian carcinoma", Future Oncol., vol. 5, No. 5, pp. 591-600, (2009), Future Medicine Ltd.

Verheul, H.M.W., et al., "Vascular Endothelial Growth Factor Trap Blocks Tumor Growth, Metastasis Formation, and Vascular Leakage in an Orthotopic Murine Renal Cell Cancer Model", Clin Cancer Res, vol. 13, No. 14, pp. 4201-4208, (2007), American Association for Cancer Research.

Mahyaoui, S., et al., "Encouraging Results of VEGF Trap (Aflibercept) Highlighted at ASCO 2007 Annual Meeting", Paris, France and Tarrytown, New York, U.S.A., (Jun. 2, 2007), 4 pages total.

Gomez-Manzano, C., et al., "VEGF Trap induces antiglioma effect at different stages of disease", Neuro-Oncology, vol. 10, pp. 940-945, (2008), Society for Neuro-Oncology.

Baffert, F., et al., "Cellular changes in normal blood capillaries undergoing regression after inhibition of VEGF signaling", Am J Physiol Heart Circ Physiol, pp. 1-46, (2005), American Physiological Society.

Fraser, H.M., et al., "Single Injections of Vascular Endothelial Growth Factor Trap Block Ovulation in the Macaque and Produce a Prolonged, Dose-Related Suppression of Ovarian Function", The Journal of Clinical Endocrinology & Metabolism, vol. 90, No. 2, pp. 1114-1122, (2005), The Endocrine Society, U.S.A.

Huang, J., et al., "Regression of established tumors and metastases by potent vascular endothelial growth factor blockade", PNAS, vol. 100, No. 13, pp. 7785-7790, (2003).

Fraser, H.M., et al., "Vascular Endothelial Growth Factor Trap Suppresses Ovarian Function at All Stages of the Luteal Phase in the Macaque", The Journal of Clinical Endocrinology & Metabolism, vol. 90, No. 10, pp. 5811-5818, (2005), The Endocrine Society, U.S.A.

Saishin, Y., et al., "VEGF-TRAPR1R2 Suppresses Choroidal Neovascularization and VEGF-Induced Breakdown of the Blood-Retinal Barrier", Journal of Cellular Physiology, vol. 195, pp. 241-248, (2003), Wiley-Liss, Inc.

Byrne, A.T., et al., "Vascular Endothelial Growth Factor-Trap Decreases Tumor Burden, Inhibits Ascites, and Causes Dramatic Vascular Remodeling in an Ovarian Cancer Model", Clinical Cancer Research, vol. 9, pp. 5721-5728, (2003).

Fukasawa, M., et al., "Vascular Endothelial Growth Factor-Trap Suppresses Tumorigenicity of Multiple Pancreatic Cancer Cell Lines", Clinical Cancer Research, vol. 10, pp. 3327-3332, (2004).

Chevalier, P., "Aflibercept (VEGF Trap) PK/PD analysis", pp. 1-25, (Jan. 10-11, 2008), Paris.

Drug Report: aflibercept (systemic, cancer), Regeneron / sanofi aventis, Thomson Pharma, pp. 1-52, (Dec. 4, 2008).

Hood, J.D., et al., "Building a better Trap", PNAS, vol. 100, No. 15, pp. 8624-8625, (2003).

Binz, H.K., et al., "Engineering novel binding proteins from nonimmunoglobulin domains", Nature Biotechnology, vol. 23, No. 10, pp. 1257-1268, (2005).

Vision Working, Regeneron Annual Report 2007, pp. 4-29, (2007).

Hu, L., et al., "Vascular Endothelial Growth Factor Trap Combined with Paclitaxel Strikingly Inhibits Tumor and Ascites, Prolonging Survival in a Human Ovarian Cancer Model", Clin Cancer Res, vol. 11, No. 19, pp. 6966-6971, (2005).

Rudge, J.S., et al., "VEGF Trap complex formulation measures production rates of VEGF, providing a biomarker for predicting efficacious angiogenic blockade", PNAS, vol. 104, No. 47, pp. 18363-18370, (2007).

Dupont, J., et al., "Phase I and pharmacokinetic study of VEGF Trap administered subcutaneously (sc) to patients (pts) with advanced solid malignancies", Journal of Clinical Oncology, 2004 ASCO Annual Meeting Proceedings (Post-Meeting Edition), vol. 22, No. 14S, Abstract No. 3009, pp. 1-9, (2004).

Fu, X., et al., "Ischemia and Reperfusion Impair the Gene Expression of Endogenous Basic Fibroblast Growth Factor (bFGF) in Rat Skeletal Muscles", Journal of Surgical Research, vol. 80, pp. 88-93, Article No. JR985349, (1998), Academic Press.

\* cited by examiner

GRPFVEMYSEIPEIIHMTEGRELVIPCRVTSPNITVTL

KKFPLDTLIPDGKRIIWDSRKGFIISNATYKEIGLLTC

EATVNGHLYKTNYLTHRQTNTIIDV*VLSPSHGIELSVG*

*EKLVLNCTARTELNVGIDFNWEYPSSKHQHKKLVNRDL*

*KTQSGSEMKKFLSTLTIDGVTRSDQGLYTCAASSGLMT*

*KKNSTFVRVHEKPFVAFGSGMESLVEATVGERVRIPAK*

*YLGYPPPEIKWYKNGIPLESNHTIKAGHVLTIMEVSER*

*DTGNYTVILTNPISKEKQSHVVSLVVYVPP* GPG*DKTHT*

*CPLCPAPELLGGPSVFLFPPKPKDTLMISRTPEVTCVV*

*VDVSHEDPEVKFNWYVDGVEVHNAKTKPREEQYNSTYR*

*VVSVLTVLHQDWLNGKEYKCKVSNKALPAPIEKTISKA*

*KGQPREPQVYTLPPSRDELTKNQVSLTCLVKGFYPSDI*

*AVEWESNGQPENNYKATPPVLDSDGSFFLYSKLTVDKS*

*RWQQGNVFSCSVMHEALHNHYTQKSLSLSPGK*

Fig. 1B

SEQUENCE LISTING

```
<160> NUMBER OF SEQ ID NOS: 8

<210> SEQ ID NO 1
<211> LENGTH: 93
<212> TYPE: PRT
<213> ORGANISM: Homo sapiens

<400> SEQUENCE: 1

Pro Phe Val Glu Met Tyr Ser Glu Ile Pro Glu Ile Ile His Met Thr
1               5                   10                  15

Glu Gly Arg Glu Leu Val Ile Pro Cys Arg Val Thr Ser Pro Asn Ile
            20                  25                  30

Thr Val Thr Leu Lys Lys Phe Pro Leu Asp Thr Leu Ile Pro Asp Gly
        35                  40                  45

Lys Arg Ile Ile Trp Asp Ser Arg Lys Gly Phe Ile Ile Ser Asn Ala
    50                  55                  60

Thr Tyr Lys Glu Ile Gly Leu Leu Thr Cys Glu Ala Thr Val Asn Gly
65                  70                  75                  80

His Leu Tyr Lys Thr Asn Tyr Leu Thr His Arg Gln Thr
                85                  90
```

```
<210> SEQ ID NO 2
<211> LENGTH: 96
<212> TYPE: PRT
<213> ORGANISM: Homo sapiens

<400> SEQUENCE: 2

Phe Ile Thr Val Lys His Arg Lys Gln Gln Val Leu Glu Thr Val Ala
1               5                   10                  15

Gly Lys Arg Ser Tyr Arg Leu Ser Met Lys Val Lys Ala Phe Pro Ser
            20                  25                  30

Pro Glu Val Val Trp Leu Lys Asp Gly Leu Pro Ala Thr Glu Lys Ser
        35                  40                  45

Ala Arg Tyr Leu Thr Arg Gly Tyr Ser Leu Ile Ile Lys Asp Val Thr
    50                  55                  60

Glu Glu Asp Ala Gly Asn Tyr Thr Ile Leu Leu Ser Ile Lys Gln Ser
65                  70                  75                  80

Asn Val Phe Lys Asn Leu Thr Ala Thr Leu Ile Val Asn Val Lys Pro
                85                  90                  95

<210> SEQ ID NO 3
<211> LENGTH: 86
<212> TYPE: PRT
<213> ORGANISM: Homo sapiens

<400> SEQUENCE: 3

Pro Arg Leu Ser Ile Gln Lys Asp Ile Leu Thr Ile Lys Ala Asn Thr
1               5                   10                  15

Thr Leu Gln Ile Thr Cys Arg Gly Gln Arg Asp Leu Asp Trp Leu Trp
            20                  25                  30

Pro Asn Asn Gln Ser Gly Ser Glu Gln Arg Val Glu Val Thr Glu Cys
        35                  40                  45

Ser Asp Gly Leu Phe Cys Lys Thr Leu Thr Ile Pro Lys Val Ile Gly
    50                  55                  60

Asn Asp Thr Gly Ala Tyr Lys Cys Phe Tyr Arg Glu Thr Asp Leu Ala
65                  70                  75                  80

Ser Val Ile Tyr Val Tyr
                85

<210> SEQ ID NO 4
<211> LENGTH: 102
<212> TYPE: PRT
<213> ORGANISM: Homo sapiens

<400> SEQUENCE: 4

Val Val Leu Ser Pro Ser His Gly Ile Glu Leu Ser Val Gly Glu Lys
1               5                   10                  15

Leu Val Leu Asn Cys Thr Ala Arg Thr Glu Leu Asn Val Gly Ile Asp
            20                  25                  30

Phe Asn Trp Glu Tyr Pro Ser Ser Lys His Gln His Lys Lys Leu Val
        35                  40                  45

Asn Arg Asp Leu Lys Thr Gln Ser Gly Ser Glu Met Lys Lys Phe Leu
    50                  55                  60

Ser Thr Leu Thr Ile Asp Gly Val Thr Arg Ser Asp Gln Gly Leu Tyr
65                  70                  75                  80

Thr Cys Ala Ala Ser Ser Gly Leu Met Thr Lys Lys Asn Ser Thr Phe
                85                  90                  95

Val Arg Val His Glu Lys
            100
```

<210> SEQ ID NO 5
<211> LENGTH: 92
<212> TYPE: PRT
<213> ORGANISM: Homo sapiens

<400> SEQUENCE: 5

Phe Val Ala Phe Gly Ser Gly Met Glu Ser Leu Val Glu Ala Thr Val
1               5                   10                  15

Gly Glu Arg Val Arg Ile Pro Ala Lys Tyr Leu Gly Tyr Pro Pro Pro
            20                  25                  30

Glu Ile Lys Trp Tyr Lys Asn Gly Ile Pro Leu Glu Ser Asn His Thr
        35                  40                  45

Ile Lys Ala Gly His Val Leu Thr Ile Met Glu Val Ser Glu Arg Asp
    50                  55                  60

Thr Gly Asn Tyr Thr Val Ile Leu Thr Asn Pro Ile Lys Ser Glu Lys
65                  70                  75                  80

Gln Ser His Val Val Ser Leu Val Val Tyr Val Pro
                85                  90

<210> SEQ ID NO 6
<211> LENGTH: 1656
<212> TYPE: DNA
<213> ORGANISM: Artificial Sequence
<220> FEATURE:
<223> OTHER INFORMATION: Recombinant DNA encoding the FP3' fusion
      protein with a signal sequence

<400> SEQUENCE: 6
atggtcagct actgggacac cggggtcctg ctgtgcgcgc tgctcagctg tctgcttctc     60
acaggatcta gttccggagg tagacctttc gtagagatgt acagtgaaat ccccgaaatt    120
atacacatga ctgaaggaag ggagctcgtc attccctgcc gggttacgtc acctaacatc    180
actgttactt taaaaaagtt tccacttgac actttgatcc ctgatggaaa acgcataatc    240
tgggacagta gaaagggctt catcatatca atgcaacgta caaagaaat agggcttctg    300 acctgtgaag caacagtcaa tgggcatttg tataagacaa actatctcac acatcgacaa    360
accaatacaa tcatagatgt ggttctgagt ccgtctcatg gaattgaact atctgttgga    420
gaaaagcttg tcttaaattg tacagcaaga actgaactaa atgtggggat tgacttcaac    480
tgggaatacc cttcttcgaa gcatcagcat aagaaacttg taaaccgaga cctaaaaacc    540
cagtctggga gtgagatgaa gaaatttttg agcaccttaa ctatagatgg tgtaacccgg    600
agtgaccaag gattgtacac ctgtgcagca tccagtgggc tgatgaccaa gaagaacagc    660
acatttgtca gggtccatga aaacctttct gttgcttttg gaagtggcat ggaatctctg    720
gtggaagcca cggtggggga gcgtgtcaga atccctgcga gtaccttgg ttacccaccc    780 ccagaaataa aatggtataa aaatggaata cccttgagt ccaatcacac aattaaagcg    840
gggcatgtac tgacgattat ggaagtgagt gaaagagaca caggaaatta cactgtcatc    900
cttaccaatc ccatttcaaa ggagaagcag agccatgtgg tctctctggt tgtgtatgtc    960
ccaccgggcc cggcgacaa aactcacaca tgcccactgt gcccagcacc tgaactcctg    1020
gggggaccgt cagtcttcct cttcccccca aaacccaagg acaccctcat gatctcccgg    1080
acccctgagg tcacatgcgt ggtggtggac gtgagccacg aagaccctga ggtcaagttc    1140
aactggtacg tggacggcgt ggaggtgcat aatgccaaga caaagccgcg ggaggagcag    1200
tacaacagca cgtaccgtgt ggtcagcgtc ctcaccgtcc tgcaccagga ctggctgaat    1260
ggcaaggagt acaagtgcaa ggtctccaac aaagccctcc cagcccccat cgagaaaacc    1320

-continued

```
atctccaaag ccaaggggca gccccgagaa ccacaggtgt acaccctgcc cccatcccgg    1380
gatgagctga ccaagaacca ggtcagcctg acctgcctag tcaaaggctt ctatcccagc    1440
gacatcgccg tggagtggga gagcaatggg cagccggaga caactacaa ggccacgcct     1500 cccgtgctgg actccgacgg ctccttcttc ctctacagca agctcaccgt ggacaagagc    1560
aggtggcagc aggggaacgt cttctcatgc tccgtgatgc atgaggctct gcacaaccac    1620
tacacgcaga agagcctctc cctgtctccg ggtaaa                              1656
```

<210> SEQ ID NO 7
<211> LENGTH: 552
<212> TYPE: PRT
<213> ORGANISM: Artificial Sequence
<220> FEATURE:
<223> OTHER INFORMATION: Synthetic construct (FP3' fusion protein with a signal sequence)

<400> SEQUENCE: 7

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
             20                  25                  30

Met Tyr Ser Glu Ile Pro Glu Ile Ile His Met Thr Glu Gly Arg Glu
         35                  40                  45

Leu Val Ile Pro Cys Arg Val Thr Ser Pro Asn Ile Thr Val Thr Leu
     50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Asn Leu Ser Val Ala Phe Gly Ser Gly Met Glu Ser Leu
225                 230                 235                 240

Val Glu Ala Thr Val Gly Glu Arg Val Arg Ile Pro Ala Lys Tyr Leu
                245                 250                 255

Gly Tyr Pro Pro Pro Glu Ile Lys Trp Tyr Lys Asn Gly Ile Pro Leu
            260                 265                 270

Glu Ser Asn His Thr Ile Lys Ala Gly His Val Leu Thr Ile Met Glu
        275                 280                 285

Val Ser Glu Arg Asp Thr Gly Asn Tyr Thr Val Ile Leu Thr Asn Pro
    290                 295                 300
```

```
Ile Ser Lys Glu Lys Gln Ser His Val Ser Leu Val Val Tyr Val
305                 310                 315                 320

Pro Pro Gly Pro Gly Asp Lys Thr His Thr Cys Pro Leu Cys Pro Ala
                325                 330                 335

Pro Glu Leu Leu Gly Gly Pro Ser Val Phe Leu Phe Pro Pro Lys Pro
            340                 345                 350

Lys Asp Thr Leu Met Ile Ser Arg Thr Pro Glu Val Thr Cys Val Val
        355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
            420                 425                 430

Leu Pro Ala Pro Ile Glu Lys Thr Ile Ser Lys Ala Lys Gly Gln Pro
        435                 440                 445

Arg Glu Pro Gln Val Tyr Thr Leu Pro Pro Ser Arg Asp Glu Leu Thr
    450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Ala Thr Pro Pro Val Leu Asp Ser Asp Gly Ser Phe Phe Leu Tyr
            500                 505                 510

Ser Lys Leu Thr Val Asp Lys Ser Arg Trp Gln Gln Gly Asn Val Phe
        515                 520                 525

Ser Cys Ser Val Met His Glu Ala Leu His Asn His Tyr Thr Gln Lys
    530                 535                 540

Ser Leu Ser Leu Ser Pro Gly Lys
545                 550

<210> SEQ ID NO 8
<211> LENGTH: 526
<212> TYPE: PRT
<213> ORGANISM: Artificial Sequence
<220> FEATURE:
<223> OTHER INFORMATION: Chimeric FP3' fusion protein

<400> SEQUENCE: 8

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110
```

Val Gly Glu Lys Leu Val Leu Asn Cys Thr Ala Arg Thr Glu Leu Asn
    115                 120                 125

Val Gly Ile Asp Phe Asn Trp Glu Tyr Pro Ser Ser Lys His Gln His
130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
                180                 185                 190

Asn Ser Thr Phe Val Arg Val His Glu Lys Pro Phe Val Ala Phe Gly
            195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
    275                 280                 285

Ser Leu Val Val Tyr Val Pro Pro Gly Pro Gly Asp Lys Thr His Thr
    290                 295                 300

Cys Pro Leu Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
    355                 360                 365

Lys Pro Arg Glu Glu Gln Tyr Asn Ser Thr Tyr Arg Val Val Ser Val
370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
    435                 440                 445

Lys Gly Phe Tyr Pro Ser Asp Ile Ala Val Glu Trp Glu Ser Asn Gly
    450                 455                 460

Gln Pro Glu Asn Asn Tyr Lys Ala Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys
    515                 520                 525

INHIBITION OF NEOVASCULARIZATION WITH A SOLUBLE CHIMERIC PROTEIN COMPRISING VEGF FLT-1 AND KDR DOMAINS

CROSS-REFERENCE TO RELATED APPLICATIONS

This application is a Continuation-In-Part of U.S. patent application Ser. No. 12/241,017, filed Sep. 29, 2008, which claims priority benefit of PCT CN2007/001021, filed Mar. 29, 2007, the disclosures of which is incorporated herein by reference in their entirety.

The Sequence Listing submitted in text format (.txt) on Dec. 19, 2011, named "Sequence_Listing.txt, (created on Dec. 19, 2011, 17 KB), is incorporated herein by reference in its entirety.

FIELD OF THE INVENTION

The present invention relates to a soluble chimeric fusion protein comprising Ig-like domain 4 of KDR, together with domain 2 of FLT-1, domain 3 of KDR and optionally, an IgG Fc sequence, as well as methods of making the soluble chimeric fusion protein, formulations, and uses thereof in treatment of conditions related to neovascularization, in particular, angiogenesis-related eye disease.

BACKGROUND OF THE TECHNOLOGY

A number of anti-angiogenic therapies that target the vascular endothelial growth factor (VEGF) ligand/receptor family are currently in development and clinical trials. VEGF stimulates division and proliferation of the endothelial cells, induces onset of neovascualrization, and provides oxygen and nutrition to the tissue cells.

A highly effective method for VEGF ligand blockade in the treatment of cancer is the use of soluble VEGF receptors such as VEGFR-1 (FLT-1) or VEGFR-2 (KDR). In the construction of these molecules, extracellular IgG-like domains of the VEGF receptors that are responsible for binding the VEGF ligand have been fused to the human IgG1 heavy chain fragment with a signal sequence at the N-terminus for secretion.

The membrane-bound tyrosine kinase receptor, known as FLT, was shown to be a VEGF receptor (DeVries, C. et al., 1992, Science, 255, pp. 989-991), which specifically binds VEGF and induces mitogenesis. Another form of the VEGF receptor, designated KDR, is also known to bind VEGF and induce mitogenesis. (Terman, B. I. et al., 1991 Oncogene 6, pp. 1677-1683; Terman, B. I. et al., 1992 Biochem. Biophys. Res. Comm. 187, pp. 1579-1586).

Persistent angiogenesis can cause neovascularization, which may result in or exacerbate eye disorders such as age-related macular degeneration, diabetic retinopathy, diseases including tumor vascularization in various cancers, psoriasis and rheumatoid arthritis.

Retinal vessels and chordial vessels are the essential components of the retina. Abnormal changes in the vessel wall structure and function of the blood vessels caused by trauma or disease can lead to hypopsia and visual loss.

Many studies have shown that once photoreceptor cells of the retina degenerate (ischemic atrophy) because of lack of nutrition, the concentration of VEGF in the retina starts to increase to promote neovascularization. This process is called angiogenesis. In the eyes, the newly generated blood vessels have different morphology from normal blood vessels in that the vessel lumen is irregular and the tissue wall is often leaky. This kind of abnormal growth of highly permeable or leaky blood vessels often results in scarring of the retina, and loss of vision.

There remains a need for clinical development of a safe and efficacious inhibitor of VEGF activity that has a favorable stability and pharmacokinetic profiles and is useful in treatment of disease associated with neovascularization, in particular, angiogenesis-related eye disease. The present invention addresses this need.

SUMMARY OF THE INVENTION

Provided herein is a method for treating an angiogenesis-related eye disease or condition, by providing a VEGF receptor fusion protein comprising Ig-like domain 4 of KDR, together with Ig-like domain 2 of FLT-1, Ig-like domain 3 of KDR and optionally, an IgG Fc sequence, exemplified herein by the fusion proteins designated FP3 and FP3', respectively, administering the fusion protein to a subject locally or intravenously, wherein one or more symptoms of the angiogenesis-related eye disease or condition is improved following said administration.

The angiogenesis-related eye disease or condition may be age-related macular degeneration (AMD), diabetic retinopathy, choroidal neovascularization (CNV), cystoid macular edema, diabetic macular edema, retinal vascular occlusion, age-related macular degeneration (AMD), diabetic retinopathy, choroidal neovascularization (CNV), cystoid macular edema, diabetic macular edema, retinal vascular occlusion, corneal neovascularization, corneal transplantation, neovascular glaucoma, pterygium, chronic conjunctivitis, angiogenesis related therapy failure such as laser coagulation, or surgical retinal transplantation.

The one or more improved symptoms of the angiogenesis-related eye disease or condition may be one or more of a decrease in mean choroidal neovascularization (CNV) leakage, improved mean visual acuity, a reduction in mean foveal retinal thickness, a reduction in mean macular size, and a reduction in mean lesion size.

Following administration of FP3 or FP3', one or more improved symptoms of the angiogenesis-related eye disease may be improved for t least 7 months.

An FP3' fusion protein may be administered by intravitreal injection, by intravenous injection, or suing eye drops.

One or more improved symptoms of an angiogenesis-related eye disease or condition including, but not limited to, a decrease in mean choroidal neovascularization (CNV) leakage, improved mean visual acuity; a reduction in mean foveal retinal thickness; a reduction in mean macular size; and a reduction in mean lesion size may be improved and remain improved for at least 7 months following administration.

The FP3' fusion protein may be provided in a formulation that comprises one or more pharmaceutically acceptable carriers commonly used for opthalmological therapeutics, either in solution or in a lyophilized form.

BRIEF DESCRIPTION OF THE DRAWINGS

FIG. 1B provides the sequence of the various components of the chimeric FP3' fusion protein (SEQ ID NO: 8), designated as FLTd2-KDRd3-KDRd4-Fc, indicating the Flt-1 D2 component (bolded); the KDR D3 component (italicized); the KDR D4 component (underlined); and the IgG Fc component (bolded and italicized).

$A=C/12\times3.1416[R^2-(R-L)^2]$, A stand for the area of area of corneal NV, C stand for the sum that blood invading area in each quadrant of the circle, L stand chimeric protein for the length of corneal NV blood vessels from limb to center of cornea.

Figure 8:
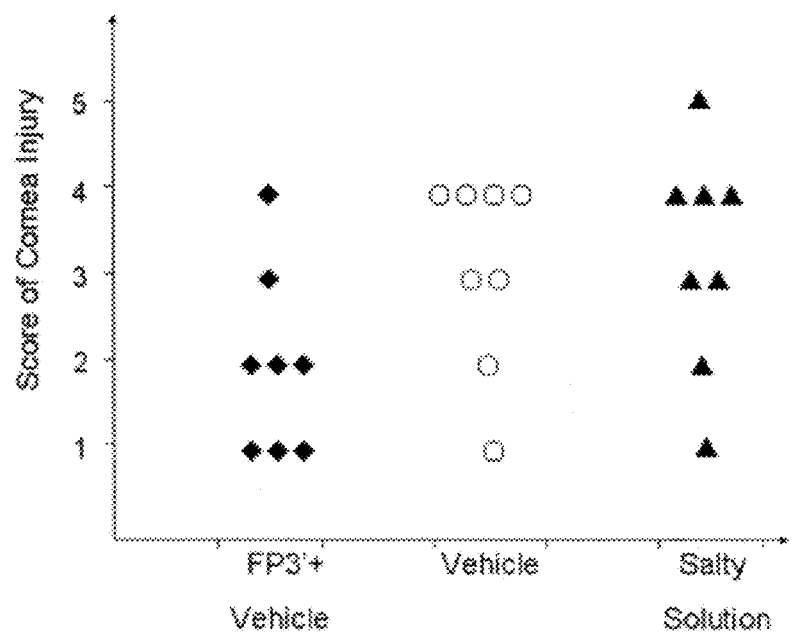

FIG. 8 illustrates the protective effect of FP3' (+vehicle) eye drops as compared to vehicle and a salty solution on cornea injury score induced by HPV-infection in mice.

Figure 9:
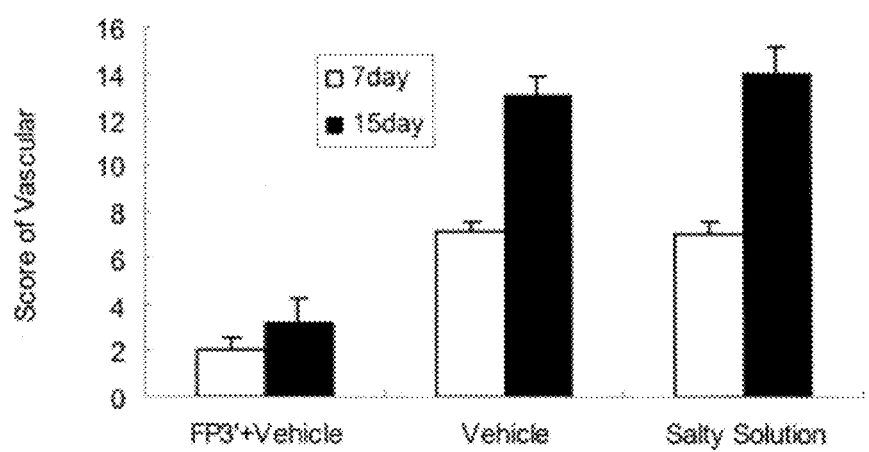

FIG. 9 illustrates the effect of FP3' (+vehicle) eye drops as compared to vehicle and a salty solution on cornea NV induced by HPV-infection in mice at 7 and 15 days post infection.

Figure 10A:
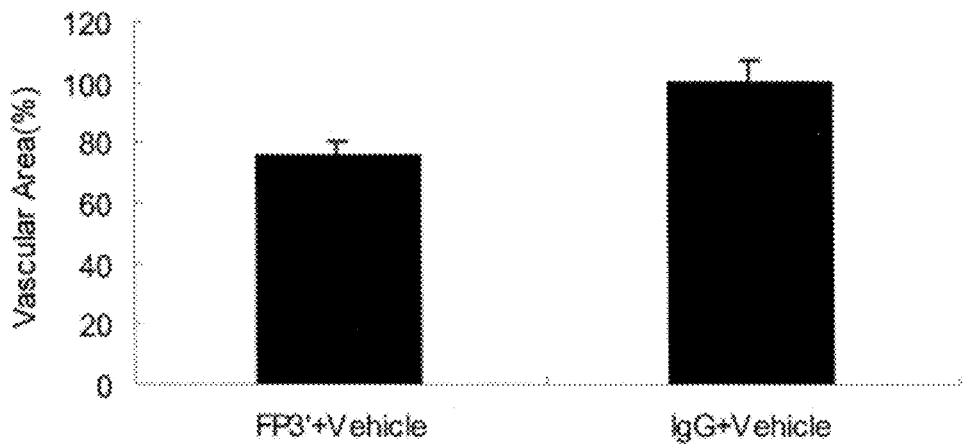

FIG. 10A illustrates the effect of FP3' (+vehicle) eye drops as compared IgG (+vehicle) eye drops on cornea vascular area (%) induced by suture placement in mice.

Figure 10B:
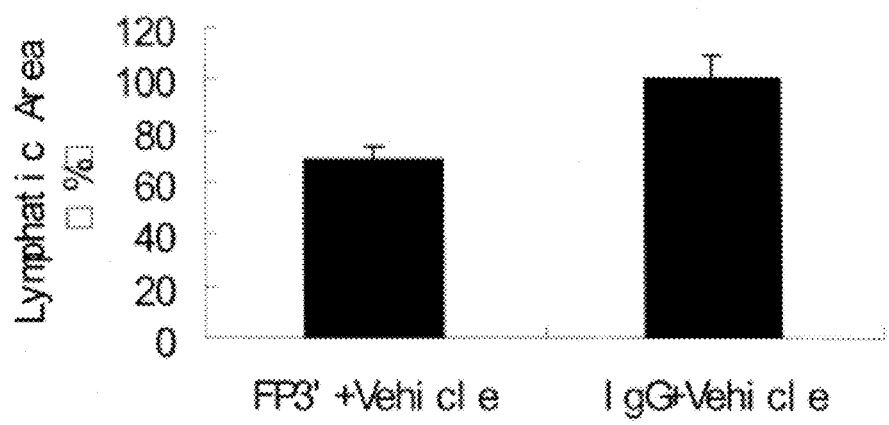

FIG. 10B illustrates the effect of FP3' (+vehicle) eye drops as compared IgG (+vehicle) eye drops on lymphangiogenesis (as indicated by lymphatic area %) induced by suture placement in mice.

Figure 11:
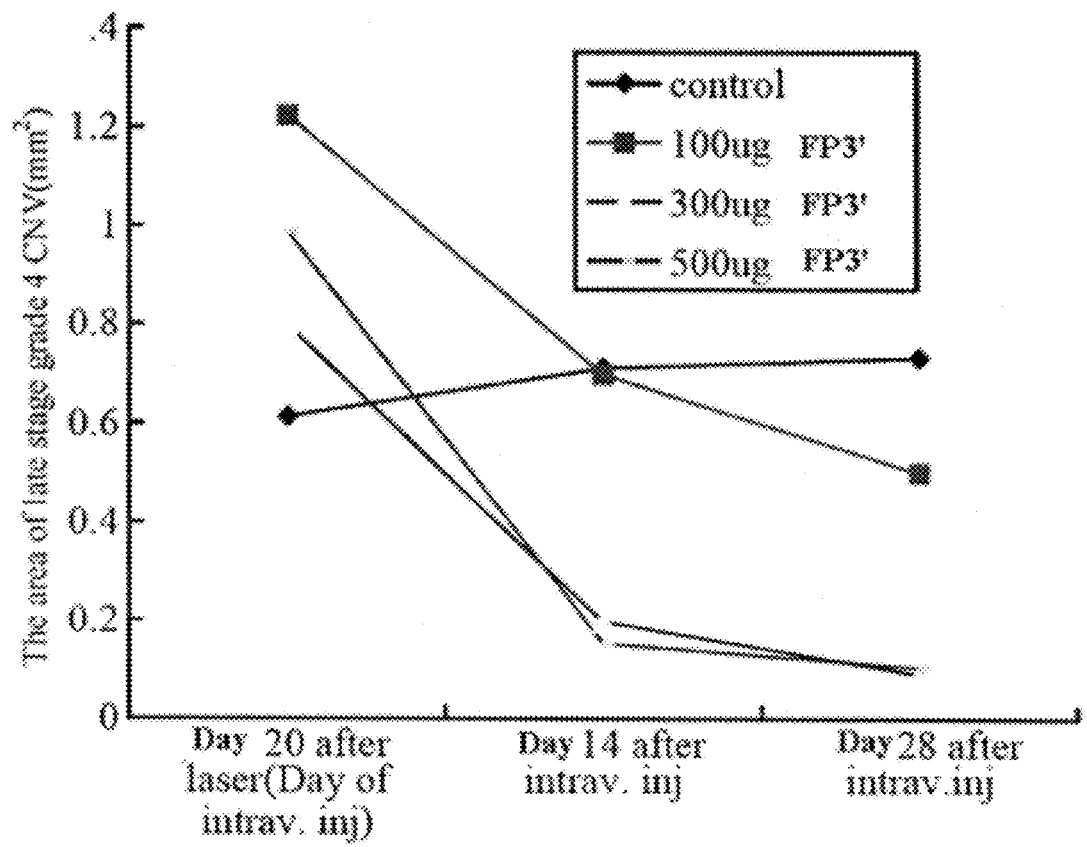

FIG. 11 provides a graphic of depiction of the mean area changes of grade 4 spots on day 20 after laser induction of CNV in the eyes of rhesus monkeys, and days 14 and 28 after intravitreal injection in control, 100 μg, 300 μg, and 500 μg FP3'-treated groups.

Figure 12:
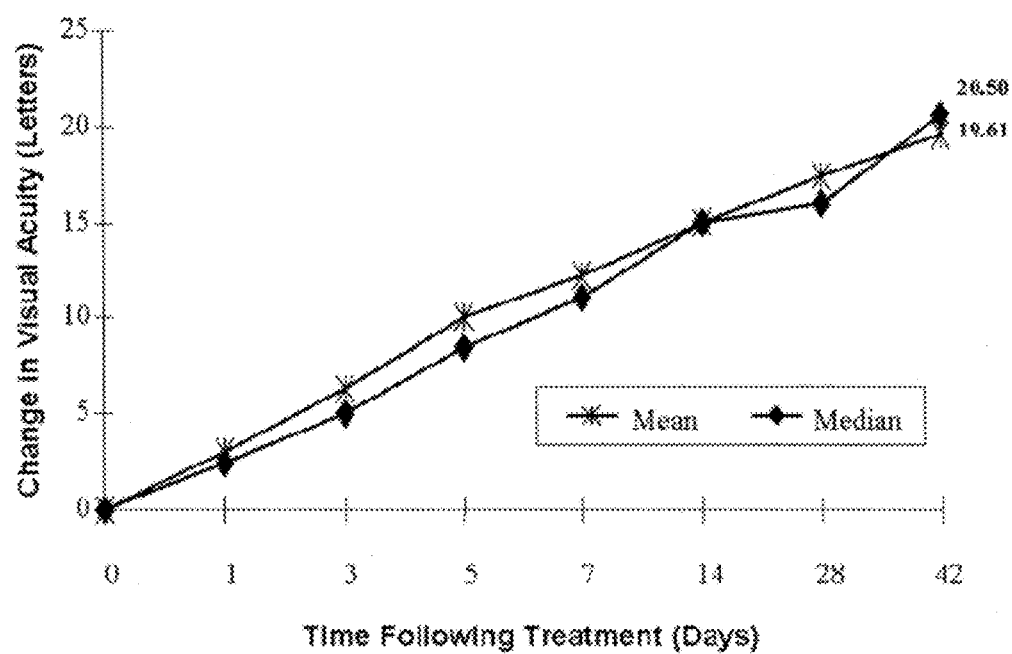

FIG. 12 provides a graphic depiction of the mean and median change in visual acuity, in terms of letters. The mean visual acuity improved from 20.57±18.13 (baseline) to 40.18±21.65 letters at day 42 following FP3' treatment.

Figure 13:
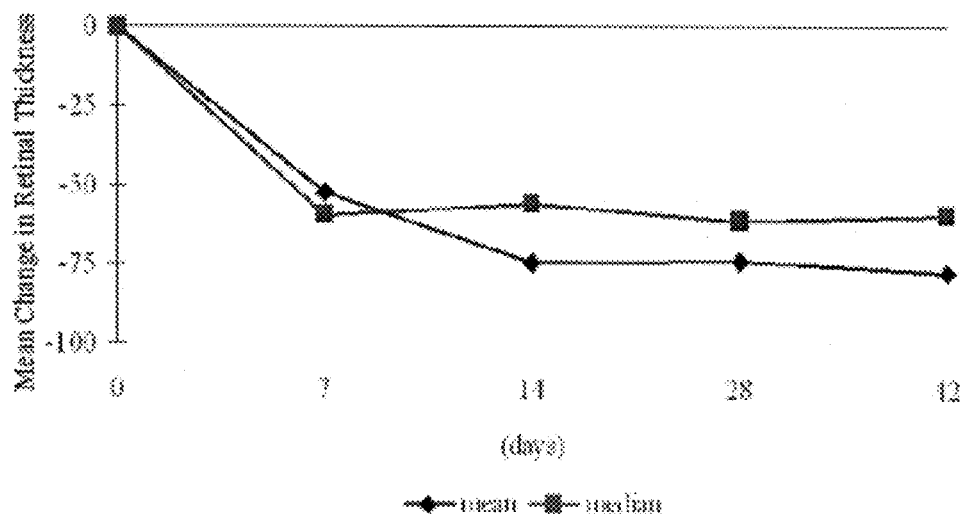

FIG. 13 provides a graphic depiction of the mean and median change in retinal thickness measured by fast OCT scan. The mean central retinal thickness was reduced from 336.54±130.45 μm (baseline) to 260.57±81.73 μm.

Figure 14:
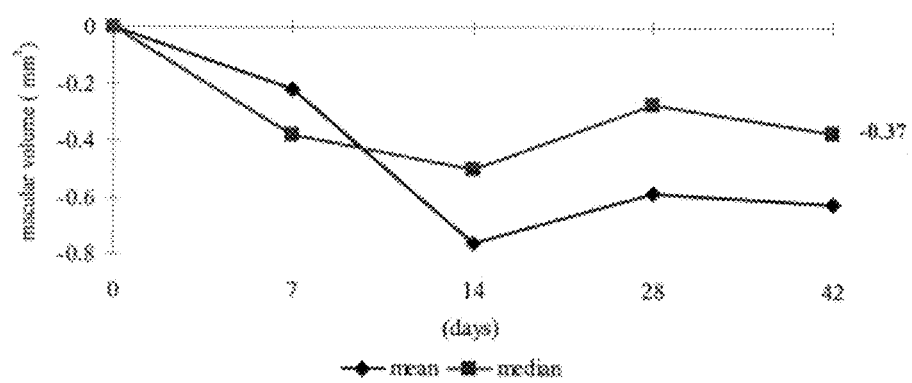

FIG. 14 provides a graphic depiction of the mean and median changes in macular volume measured by fast OCT scan. The mean macular volume was decreased from 7.53±1.69 mm$^3$ (baseline) to 6.97±0.97 mm$^3$.

Figure 15:
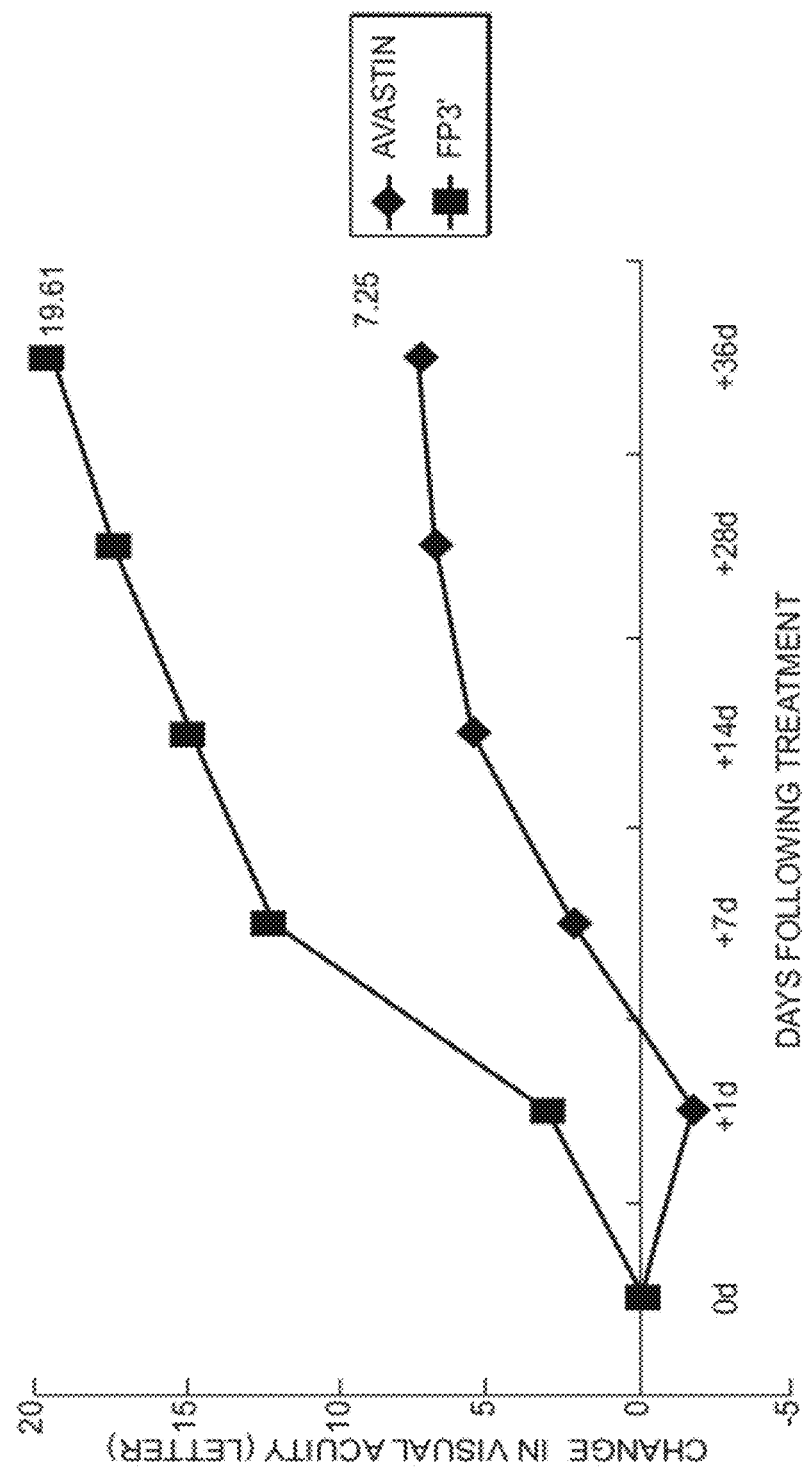

FIG. 15 provides a graphic depiction of the effect of FP3' and Avastin on mean visual acuity in patients with age-related macular degeneration.

DETAILED DESCRIPTION OF THE INVENTION

The following disclosure is generally directed to a soluble chimeric fusion protein, designated FP3 or FP3', comprised of Ig-like domain 4 of KDR, together with domain 2 of FLT-1, domain 3 of KDR and, optionally an IgG Fc sequence, methods of making and using the fusion proteins, variants thereof, and formulations comprising the fusion protein.

A number of chimeric proteins containing different fragments of the VEGF receptors, FLT-1 and KDR, were constructed using conventional molecular cloning technologies routinely used by those of skill in the art. See, e.g., US Patent Publication No. 2008/0206238 and U.S. Ser. No. 12/241,017, both of which are expressly incorporated by reference herein. FP3/FP3' was selected based on stability of clonal expression and biological activity in a number of in vitro assays, with the biological activity confirmed in clinical studies in vivo in humans and monkeys.

The invention is not limited to the specific sequences, compositions, systems and methodology or syndromes described herein, as these may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug formulations and devices for containment, storage and delivery of such formulations.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

The practice of the present invention employs, unless otherwise indicated, conventional techniques of chemistry, molecular biology, microbiology, recombinant DNA, genetics, immunology, cell biology, cell culture and transgenic biology, which are within the skill of the art.

Definitions

As used herein, the terms "soluble chimeric fusion protein" and "chimeric fusion protein" may be used interchangeably and refer to proteins comprising a fusion between two or more protein domains linked to a dimerizing or multimerizing domain (such as IgGFc), wherein the soluble chimeric fusion protein targets two or more receptors or pathways related to angiogenesis. By domain is meant a part of protein sequence and structure that can function, and exist independently of the rest of the protein chain.

As used herein, "VEGF" refers to vascular endothelial growth factor a sub-family of the platelet-derived growth factor family of cysteine-knot growth factors that are involved in both vasculogenesis (de novo formation of the embryonic circulatory system) and angiogenesis (the growth of blood vessels from pre-existing vasculature. All members of the VEGF family stimulate cellular responses by binding to tyrosine kinase receptors (VEGF receptors of VEGFRs) on the cell surface, causing them to dimerize and become activated. The VEGF receptors have an extracellular portion consisting of 7 immunoglobulin-like domains, a single transmembrane spanning region and an intracellular portion. VEGF-A binds to VEGFR-1 (Flt-1) and VEGFR-2 (KDR/Flk-1). VEGFR-2 appears to mediate almost all of the known cellular responses to VEGF.

The terms "FLT-1" or "VEGFR1", as used herein, refer more specifically to a fms-like tyrosine kinase receptor, also known as vascular endothelial growth factor receptor 1.

The terms "KDR" or "FLK-1" or "VEGFR2", as used herein, refer more specifically to kinase insert domain-containing receptor or fetal liver kinase or vascular endothelial growth factor receptor 2.

Figure 1A:
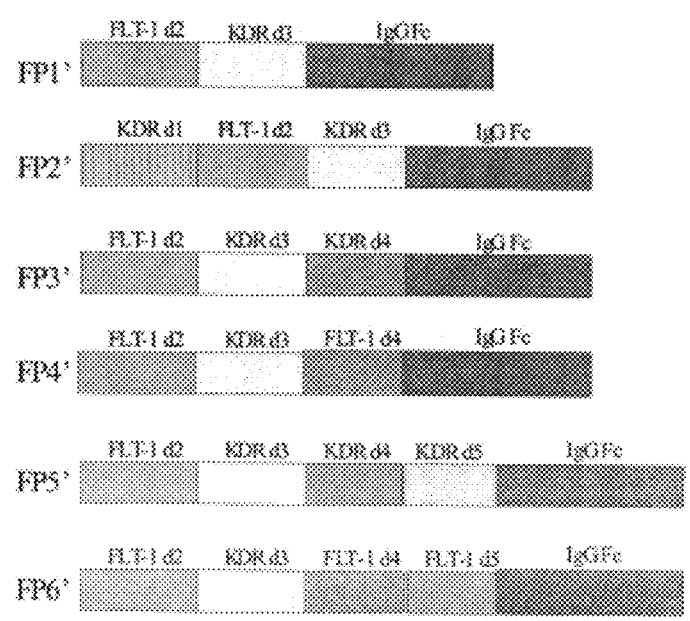
FIG. 1A provides a schematic depiction of FP1' (the chimeric protein known in the art as VEGF-TRAP), consisting of the $2^{nd}$ Ig-like domain of FLT-1 (FLTd2), the $3^{rd}$ Ig-like domain of KDR (KDRd3), and human immunoglobulin Fc (IgFc)-FLTd2KDRd3-Fc; FP2' designated as KDRd1-FLTd2-KDRd3-Fc; FP3' designated as FLTd2-KDRd3-KDRd4-Fc; FP4' designated as FLTd2-KDRd3-FLTd4-Fc; FP5' designated as FLTd2-KDRd3-KDRd4-KDRd5-Fc; and FP6' designated as FLTd2-KDRd3-FLTd4-FLTd5-Fc. When each molecule is constructed without the IgFc component, it has the same name, but lacks the "'" designation, i.e., FP1, FP2, FP3, FP4, FP5 and FP6, respectively.

As used herein, the term "immunoglobulin domain" or "Ig-like domain" refers to each of the independent and distinct domains that are found in the extracellular ligand region of the claimed soluble chimeric fusion proteins. The "immunoglobulin-like domain" or "Ig-like domain" refers to each of the seven independent and distinct domains that are found in the extracellular ligand-binding region of the Flt-1 and KDR receptors. Ig-like domains are generally referred to by number, the number designating the specific domain as shown in FIG. 1A.

As used herein, the term "Ig-like domain" is intended to encompass not only the complete wild-type domain, but also insertional, deletional and substitutional variants thereof which substantially retain the functional characteristics of the intact domain. It will be readily apparent to those of ordinary skill in the art that numerous variants of Ig-like domains can be obtained which retain substantially the same functional characteristics as the wild type domain.

The term "multimerizing domain" or "multimerizing component" as used herein refers to a domain, such as the Fc domain from an IgG that is heterologous to the binding domains of the claimed soluble chimeric fusion proteins. A multimerizing domain may be essentially any polypeptide that forms a dimer (or higher order complex, such as a trimer, tetramer, etc.) with another polypeptide. Optionally, the multimerizing domain associates with other, identical multimerizing domains, thereby forming homomultimers. An IgG Fc element is an example of a dimerizing domain that tends to form homomultimers. As used herein the term multimerizing domain may be used to refer to a dimerizing, trimerizing, tertramerizing domain, etc. Fc refers to the human immunoglobulin Fc fragment derived from human immunoglobulin FC such as IgG, IgM, and IgA, or subclasses IgG1, IgG2, IgG3, and IgG4. The Fc region can be the full length Fc sequence or a fragment of the Fc sequence from CH2, CH3, or the hinge region. The Ig-like domain of interest is typically fused to the N-terminus of the Fc domain of immunoglobulin G1 (IgG1). In some cases, the entire heavy chain constant region is fused to the VEGF receptor Ig-like domains of interest. However, more preferably, a sequence beginning in the hinge region just upstream of the papain cleavage site which defines Fc chemically, or analogous sites of other immunoglobulins are used in the fusion.

As used herein, the term "FP3'" refers to a particular chimeric fusion protein comprising domain 2 of the VEGF receptor FLT-1; domains 3 and 4 of KDR; and a human immunoglobulin G (IgG) Fc sequence linked by spacers. "FP3" is sued with reference to the chimeric fusion protein comprising domain 2 of the VEGF receptor FLT-1; domains 3 and 4 of KDR, which lacks a human immunoglobulin G (IgG) Fc sequence.

FP3' is designated as FLTD2-KDRD3,4-FC and has a total of 526 amino acids (FIG. 1B,; SEQ ID NO: 8). SEQ ID NO:7 shows the amino acid sequence of FP3' with a signal sequence, resulting in a total of 552 amino acids. The FLT-1d2 component of FP3' is 93 amino acids (SEQ ID NO:1); the KDRd3 component of FP3' is 102 amino acids (SEQ ID NO:4) and the KDRd4 component of FP3' is 92 amino acids (SEQ ID NO:5). The IgGFc component of FP3' is 236 amino acids. Domain 4 of KDR corresponds to amino acids 328 to 421 of full length receptor (1356 amino acids). See, e.g., GenBank Accession Nos. ACF47599.1; AAC16450.1; NP_002244.1; and AAI31823. The DNA coding sequence of the amino acid sequence of SEQ ID NO.7 is presented as SEQ ID NO:6.

As used herein, the term "neovascularization" is defined as proliferation of blood vessels in tissue not normally containing them or proliferation of blood vessels of a different kind than typically present in a particular tissue.

As used herein, the term "ligand-binding domain" of a protein is that portion of the protein which is involved with binding the natural ligand.

The term "extracellular ligand binding domain" is defined as the portion of a receptor that, in its native conformation in the cell membrane, is oriented extracellularly where it can contact with its cognate ligand. The extracellular ligand binding domain does not include the hydrophobic amino acids associated with the protein's transmembrane domain or any amino acids associated with the protein's intracellular domain.

The term "soluble" as used herein with reference to the claimed chimeric fusion proteins is intended to mean chimeric proteins which are not fixed to the surface of cells via a transmembrane domain. As such, while the mechanism is not part of the invention, soluble forms of the claimed chimeric fusion proteins, while capable of binding to and inactivating VEGF, do not comprise a transmembrane domain and thus generally do not become associated with the cell membrane of cells in which the molecule is expressed.

The term "membrane-bound" as used herein with reference to the soluble fusion proteins is intended to mean chimeric proteins that are fixed, via a transmembrane domain, to the surface of cells in which they are expressed.

The term "native" refers to a gene that is present in the genome of the wild type virus or cell.

The term "naturally occurring" or "wild type" is used to describe an object that can be found in nature as distinct from being artificially produced by man. For example, a protein or nucleotide sequence present in an organism, which can be isolated from a source in nature and which has not been intentionally modified by man in the laboratory, is naturally occurring.

The term "recombinant" as used herein with reference to nucleotide sequences refers to a combination of nucleotide sequences that are joined together using recombinant DNA technology into a progeny nucleotide sequence. As used herein with reference to viruses, cells, and organisms, the terms "recombinant," "transformed," and "transgenic" refer to a host virus, cell, or organism into which a heterologous nucleotide sequence has been introduced. The nucleotide sequence can be stably integrated into the genome of the host or the nucleotide sequence can also be present as an extrachromosomal molecule. Recombinant viruses, cells, and organisms are understood to encompass not only the end product of a transformation process, but also recombinant progeny thereof. A "non-transformed," "non-transgenic," or "non-recombinant" host refers to a wild type virus, cell, or organism that does not contain the heterologous nucleotide sequence.

The term "operatively linked" relates to the orientation of polynucleotide elements in a functional relationship. Operatively linked means that the DNA sequences being linked are generally contiguous and, where necessary to join two protein coding regions, contiguous and in the same reading frame. However, since enhancers generally function when separated from the promoter by several kilobases and intronic sequences may be of variable length, some polynucleotide elements may be operatively linked but not contiguous.

The term "vector", as used herein, refers to a nucleotide sequence or construct designed for transfer between different host cells. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector. Any vector for use in gene introduction can basically be used as a "vector" into which the DNA having the desired sequence is to be introduced. Plasmid vectors will find use in practicing the present invention. The term vector as it applies to the present invention is used to describe a recombinant vector, e.g., a plasmid or viral vector (including a replication defective or replication competent virus) or any construct for gene transfer, as understood by one skilled in the art.

The term "homologous" as used herein with reference to nucleotide molecule refers to a nucleotide sequence naturally associated with a host virus or cell.

The terms "identical" or percent "identity" are used herein in the context of two or more nucleotide sequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

As used herein, the term "sequence identity" refers to the degree of identify between nucleotides in two or more aligned sequences, when aligned using a sequence alignment program. The term "% homology" is used interchangeably herein with the term "% identity" herein and refers to the level of nucleotide or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

The terms "administering" or "introducing", as used herein refer to the direct application of a drug, whether by topical application, injection, inhalation, ingestion, or any other means or delivery to a person or an animal."

The term "DUXB11 cells" is used herein with reference to a CHO cell line that is deficient in DHFR.

The term "Human Umbilical Vein Endothelial Cells" (HUVECs), is used herein with reference to cells derived from a HUVEC clone (e.g., Cascade Biologic™) isolated from normal human umbilical vein, cryopreserved at the end of primary culture. HUVECs are responsive to cytokine stimulation in the expression of cell adhesion molecules and are used in assays of angiogenesis.

The term "Hep3B cells" is used herein with reference to cells used in an orthotopic xenograft tumor model of hepatocellular carcinoma in nude mice.

The term "A549 cells" is used herein with reference to lung adenocarcinoma cells used in an used in a xenograft solid tumor model in nude mice.

The term "Lovo cells" is used herein with reference to colon carcinoma cells used in a xenograft model in nude mice.

The term "MCF-7 cells" is used herein with reference to the MCF-7 human breast carcinoma cell line used in a xenograft model in nude mice.

An "individual" is a vertebrate, a mammal, or a human. Mammals include, but are not limited to, farm animals, sport animals, rodents, primates, and pets.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

As used herein, the term "angiogenesis-related eye disease" is used with reference to conditions including, but not limited to, AMD, diabetic retinopathy, cystoid macular edema, diabetic macular edema, retinal vascular occlusion, angiogenesis related therapy failure such as laser coagulation, and surgical retinal transplantation.

As used herein, the terms "biological activity" and "biologically active", refer to the activity attributed to a particular protein in a cell line in culture or in vivo.

As used herein, the term therapeutically effective amount" of a claimed soluble chimeric fusion protein is an amount that is effective to either prevent, lessen the worsening of, alleviate, or cure the treated condition, in particular that amount which is sufficient to reduce or inhibit the proliferation of vascular endothelium in vivo.

As used herein, the terms "neoplastic cells", "neoplasia", "tumor", "tumor cells", "carcinoma", "carcinoma cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

Soluble Chimeric Fusion Proteins

Ig-like Domains

The claimed soluble fusion proteins are comprised of at least two Ig-like domains that bind at least two different angiogenic factor. The soluble fusion protein may also contain a multimerizing domain. The precise site at which the fusion is made is not critical; particular sites are well known and may be selected in order to optimize the biological activity, secretion, bioavailability or binding characteristics of the protein.

Examples of the claimed FP3' chimeric fusion proteins are described throughout the specification and particularly in the examples and in FIG. 1B. Ig-like domains are known and recognized by those skilled in the art.

VEGF (Vascular Endothelial Growth Factor)

A number of strategies aimed at blockage of the VEGF pathway are in clinical development. Blockage of the VEGF pathway has been achieved by a number of approaches such as blocking antibodies targeted against VEGF (Asano, M., et al. (1998) Hybridoma 17, 185-190) or its receptors (Prewett, M. et al. (1999) Cancer Res. 59, 5209-5218), soluble decoy receptors that prevent VEGF from binding to its normal receptors, as well as chemical inhibitors of the tyrosine kinase activity of the VEGFRs. A study that compared the efficacy of VEGF blockade to other "antiangiogenic" strategies established that this approach is superior to many others. (See, e.g., Holash et al. PNAS, 99 (17) 11393, 2002; WO 00/75319.)

There are at least three recognized VEGF receptors: VEGFR1, VEGFR2 and VEGFR3. VEGFR1 is also called Flt-1, whose biological function is not well defined yet. Vascular Endothelial Growth Factor receptor 1 is also called fms-related tyrosine kinase 1 (FLT1), and vascular endothelial growth factor/vascular permeability factor receptor. VEGFR2 is a transmembrane tyrosine kinase receptor, consisting of an Ig-like extracellular domain, a hydrophobic transmembrane domain, and an intracellular domain containing two tyrosine kinase motifs. VEGFR3 plays a key role in lymphatic angiogenesis. VEGFR3 binds VEGF-C and -D.

Vascular Endothelial Growth Factor (VEGF) mediates its actions through the VEGF receptor 1 (Flt-1) and VEGF receptor 2 (KDR or Flk-1) receptor tyrosine kinesis. To localize the extracellular region of Flt-1 that is involved in ligand interactions, secreted Fc fusion proteins between the extracellular ligand biding domain of the receptor and IgG1 Fc have been generated and evaluated for VEGF-A and PIG-1 affinity (Cunningham et al. 1997. Biochem Biophys Res Commun. 1997 Feb. 24; 231 (3):596-9; Ma L et al. Biotechnol Appl Biochem. 34 (Pt 3):199-204, 2001; Holash et al. Proc Natl Acad Sci USA. August 20; 99 (17):11393-8 (2002)). Ligand binding studies show that amino acids 1-234 are sufficient to achieve minimal VEGF-A (VEGF 165 isoform) interactions. The extension of this region to 1-331 amino acids (SEQ ID NO:3) provides high affinity ligand binding comparable to the full receptor. This region is also sufficient to achieve interactions of Flt-1 with Placental Growth Factor (PIGF-1). VEGFR1 binds VEGF-A and -B.

VEGFR2 is also called KDR in human and Flk-1 for its mouse homologous. VEGFR2 (KDR/FLK-1) is a ~210 kDa member of a receptor tyrosine kinase family whose activation plays a role in a large number of biological processes such as embryonic development, wound healing, cell proliferation, migration, and differentiation. VEGFR2 expression is mostly restricted to vascular endothelial cells. VEGFR2 binds VEGF-A and -B. The extracellular region of KDR consists of seven immunoglobulin-like domains, and deletion studies have shown that amino acids 1-327 are sufficient and necessary for high affinity binding to VEGF (Kaplan et al. 1997; Fu et al 1998). Deletion of amino acids 224-327 from this construct reduced the binding to VEGF by >1000-fold, indicating a critical functional role for this region in VEGF/KDR interaction. Results suggest that VEGFR-3 needs to be associated to VEGFR-2 to induce ligand-dependent cellular responses (Alam A. et al., Biochem Biophys Res Commun. 2004 Nov. 12; 324 (2):909-15).

One method for VEGF ligand blockade is the use of soluble VEGF receptors such as those derived from VEGFR-1 or VEGFR-2. Such molecules may be constructed by fusing the extracellular IgG-like domains of the VEGF receptors that are responsible for binding the VEGF ligand, to the human IgG1 heavy chain fragment with a signal sequence at the N-terminus for secretion. Given the high degree of amino acid homology between Flt-1 and KDR, corresponding regions of amino acids between the 2 receptors can substitute when swapped between the molecules and in such a manner, create molecules with altered binding affinities. For example the KDR/Flt-1 hybrid VEGF-Trap. VEGF (Vascular Endothelial Growth Factor) Trap is a composite decoy receptor fusion protein that contains portions of the extracellular domains of two different VEGF receptors VEGFR-1 (flt-1) and VEGFR-2 (KDR). The VEGF Trap (R1R2) has a high affinity for VEGF. See, e.g., Holash et al. Proc Natl Acad Sci USA. August 20; 99 (17):11393-8 (2002); U.S. Pat. Nos. 7,070,959; 7,279,159; 7,087,411 and U.S. Patent Publication Nos. 20090081217 and 20090062200. Chimeric VEGF receptors which are chimeras of derived from VEGFR-2 and VEGFR-3 are described for example in WO02/060950.

Provided herein are soluble chimeric fusion proteins comprising a fusion between domain 2 of the VEGF receptor FLT-1; domains 3 and 4 of KDR; and a human immunoglobulin G (IgG) Fc sequence (which serves as a dimerizing or multimerizing domain), referred to herein as "FP3" or "FP3'".

As a method for prolonging the plasma half-life, it is known to utilize a fusion protein or polypeptide genetically engineered by combining the protein or polypeptide of interest with a molecule having a long plasma half-life, such as an antibody molecule.

Sequence Variants

There is no absolute boundary of the amino acid sequences of the Ig-like domains of FLT-1 and KDR, and the sequence length of these domains can have variations. Thus the sequences of the chimeric proteins described here may have similar variations. It should be appreciated that these sequence variants are not to be considered as beyond the scope of the invention.

Binding of the ligand is not be the only variable that is important to the function of the claimed soluble chimeric fusion proteins, since other factors such as the secretion of the receptor from the cell, dimerization and bioavailability are also important.

It is understood that variants or mutants of the Ig-like domains that bind to an angiogenic factor(s) find use in the present invention. For both in vivo and in vitro applications, in order to inhibit angiogenesis, the claimed soluble chimeric fusion proteins need to be available for binding to the angiogenic factors. It is believed that positive charges on proteins allow proteins to bind to extracellular matrix components and the like, possibly reducing their availability to bind their ligand (e.g. angiogenic factor). Therefore, provided herein are soluble chimeric fusion proteins that are modified to reduce the positive charges (e.g. lower the pl). There are methods known to those skilled in the art for modifying the charge of a protein including acetylation and/or by replacing codons of the coding region that code for positive charged amino acids with codons for neutral or negatively charged amino acids. Examples of these types of modifications are described for example in WO200075319. Various amino acid substitutions can be made in the Ig-like domain or domains without departing from the spirit of the present invention with respect to the proteins' ability to bind to angiogenic factors and inhibit angiogenesis. Thus point mutations and broader variations may be made in the Ig-like domain(s) so as to impart interesting properties that do not substantially affect the chimeric protein's ability to bind angiogenic factors and inhibit angiogenesis. Sequence variants encoding the Ig-like domains of the claimed soluble fusion proteins are included within the scope of the invention.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Gene Delivery Vectors The claimed chimeric proteins can be obtained through conventional recombinant DNA technologies. At first, recombinant DNA coding sequences of the above mentioned chimeric proteins are obtained. The DNA sequences of FLT-1 and KDR are available in GenBank, NCBI (National Center for Biotechnology Information). The DNA coding sequences of the above-mentioned chimeric proteins are cloned into vectors. The vectors may be commonly used plasmids, viruses, or DNA fragments in molecular biology. Vector production may be accomplished by any known method routinely employed by those of skill in the art.

The claimed vectors may, in addition to coding for the claimed soluble chimeric fusion proteins, may include one or more other transgenes. Also, the claimed vectors and/or chimeric soluble fusion proteins may be used in combination with vectors encoding other transgenes.

Vectors and Methods for Expression of FP3'

Vector constructs comprising nucleotide sequences encoding chimeric soluble PF3' fusion proteins may be introduced into cells in vitro, ex vivo or in vivo for delivery of chimeric soluble fusion proteins to cells, e.g., somatic cells, or in the production of recombinant soluble fusion proteins by vector-transduced cells using standard methodology known in the art.

Viral vector particles may be utilized for the purpose of transferring DNA, RNA or other nucleic acids into cells either in vitro or in vivo. Numerous forms of viral and non-viral vectors are known in the art. Exemplary vectors that may be utilized for practicing the invention include, but are not limited to, e.g. derived from MoMLV, MSCV, SFFV, MPSV, SNV etc), including lentiviruses (e.g. derived from HIV-1, HIV-2, SIV, BIV, FIV etc.), vaccinia virus vectors, herpes virus vectors (e.g., HSV), baculoviral vectors, cytomegalovirus (CMV) vectors, papillomavirus vectors, simian virus (SV40) vectors, Sindbis vectors, Rous sarcoma virus vectors semliki forest virus vectors, phage vectors, Epstein Barr virus vectors, herpes virus vectors adenovirus (Ad) vectors including replication competent, replication deficient and gutless forms thereof, baculovirus vectors, adeno-associated viral (AAV) vectors, nonviral plasmid vectors (introduced by electroporation, sonoporation, or use of a "gene gun"), lipoplexes or polyplexes; liposome-encapsulated DNA, virosomes or dendrimers.

The vectors or constructs for expression of PF3', may be introduced into cells using standard methodology. Methods for transfection, transduction or infection are well known by those of skill in the art. The term "transduction" refers to the delivery of a nucleic acid molecule into a recipient cell either in vivo or in vitro via infection, internalization, transfection or any other means. Transfection may be accomplished by a variety of means known in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics, as generally known in the art. Such techniques can be used to introduce one or more exogenous DNA moieties, such as a plasmid vector and other nucleic acid molecules, into suitable host cells. The term refers to both stable and transient uptake of the genetic material.

Vectors utilized in practicing the invention may optionally code for a selectable marker, such as neo, DHFR, Gln synthetase or ADA, followed by selection in the presence of the appropriate drug and isolation of clones. More than one vector may be used to introduce the coding sequences for PF3' into a cell. The invention is not limited to any sequential order for transduction. In other words, more than one vector may be used essentially simultaneously or sequentially in any order to transduce the cells.

For in vitro or ex vivo expression, any cell effective to express a functional soluble fusion protein may be employed. Numerous examples of cells and cell lines used for protein expression are known in the art. For example, prokaryotic cells and insect cells may be used for expression. In addition, eukaryotic microorganisms, such as yeast may be used. The expression of recombinant proteins in prokaryotic, insect and yeast systems are generally known in the art and may be adapted for antibody expression using the compositions and methods disclosed herein.

Examples of cells useful for soluble chimeric fusion protein expression further include mammalian cells, such as fibroblast cells, cells from non-human mammals such as ovine, porcine, murine and bovine cells, insect cells and the like. Specific examples of mammalian cells include Chinese hamster ovary (CHO) cells, 293 cell, NSO cells, SP20 cells, 3T3 fibroblast cells, W138 cells, BHK cells, HEPG2 cells, DUX cells, COS cells, VERO cells, HeLa cells and MDCK cells.

In one embodiment, the cells can be maintained in culture for a number of replications and genetically altered, if necessary. In one embodiment, the cell is a neoplastic cell, a malignantly transformed cell, or the progeny of such cells. Cells may be deliberately transformed into long-lived cell lines by any method, including, but not limited to, fusion with other cell lines, treatment with a chemical carcinogen, infection with a suitable virus such as Epstein-Barr virus or oncogenic virus, or transduced with a coding region that codes for a protein that allows continuous propagation (e.g. large T-antigen from SV40).

Host cells are cultured in conventional nutrient media, modified as appropriate for inducing promoters, selecting transformants, or amplifying the genes encoding the desired sequences. Mammalian host cells may be cultured in a variety of commercially. A given medium is generally supplemented as necessary with hormones and/or other growth factors (such as insulin, transferrin, or epidermal growth factor), DHFR, salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The appropriate culture conditions for a particular cell line, such as temperature, pH and the like, are generally known in the art, with suggested culture conditions for culture of numerous cell lines provided, for example, in the ATCC Catalogue available on line at <"http://www.atcc.org/Search catalogs/AllCollections.cfm">.

A vector encoding the claimed soluble chimeric fusion proteins may be administered in vivo via any of a number of routes (e.g., intradermally, intravenously, intratumorally, into the brain, intraportally, intraperitoneally, intramuscularly, into the bladder etc.), effective to deliver the vector in animal models or human subjects. Dependent upon the route of administration, the recombinant soluble chimeric fusion protein will elicit an effect locally or systemically. The claimed recombinant vectors can be administered using conventional modes of administration including but not limited to the modes described above and may be in a variety of formulations which include but are not limited to liquid solutions and suspensions, microvesicles, liposomes and injectable or infusible solutions. The preferred form depends upon the mode of administration and the therapeutic application.

As the experimental results provided herein show, there are many advantages in using recombinant vector constructs encoding the claimed soluble fusion proteins in the in vitro production of recombinant protein for direct administration to a patient. Methods for recombinant protein production are well known in the art and may be utilized for expression of recombinant soluble chimeric fusion protein using the vector constructs described herein.

Purification of FP3' Fusion Protein

The fusion protein may be produced by large scale culture, followed by enrichment, i.e., clarification by depth filtration, initial capture by affinity chromatography, e.g., using protein A resin, followed by elution and further purification and polishing. The further purification and polishing steps may include cation exchange chromatography, a multimodal medium, such as Capto™ adhere, size exclusion chromatography (SEC), a Mustang Q membrane (Pall Biopharmaceuticals) and/or passage through a nanofilter with nominal pore size of 20 nm using a validated virus inactivation process. The purified protein is then sterile filtered using a 0.2 μm membrane filter, aliquoted, and kept at 4° C. or frozen for long term storage.

Upon purification to pharmaceutical grade, following confirmation of biological activity by in vitro analysis (as detailed herein below), the recombinant FP3' fusion protein can be mixed with conventional pharmaceutical acceptable carriers and/or adjuvants to obtain the desired formulation for in vivo administration.

Compositions and Methods of Administration of FP3'

Recombinant FP3' fusion protein can be formulated for intravitreal or intravenous injection to treat various angiogenesis-related eye diseases including AMD, diabetic retinopathy, diabetic macular edema and central retinal vein occlusion.

Stability of FP3' formulations following storage for varying lengths of time at different temperatures was carried out to verify the stability of the FP3' fusion protein, as detailed in Examples 4A and 4B.

Recombinant FP3' fusion protein can be formulated for use in intravenous administration, intravitreal administration, intraperitoneal administration, subcutaneous administration and topical ocular administration (e.g., as eye drops). In one preferred approach, FP3' is provided as a solution formulation or lyophilized such that it can be reconstituted prior to use.

The fusion protein is typically provided in a formulation which comprises one or more of the following: sodium phosphate, sodium succinate, histidine, mannitol, trehalose dehydrate, polysorbate 20, sodium chloride, sucrose, tromeramol, cellulose, modified cellulose or lactose. The aforementioned formulations can contain pH formulation buffers such as phosphate, citrate, acetate, succinate, tromeramol (Tris), histidine or any combination thereof, with concentrations of 0-100 mM, e.g., 1-100 mM, and pH ranging from 3-9; and can also contain osmoregulators such as sodium chloride (concentration ranging from 1 to 200 mM, e.g. 1-100 mM), dextrose (concentration ranging from 0% to 50%, e.g. 1-30%); and can stabilizer such as amino acids, glycerol, cyclodextrin, sucrose, trehalose, dehydrate with concentrations 0%-40%, preferably 1-30%; and can contain preservatives such as thimerosal, sodium bisulfate, benzyl alcohol, etc. In lyophilized formulations, excipients such as mannitol may be included at a concentration of from about 0.001% to 40%, preferably 0.1% to 10%. In solution formulations, surfactants such as polysorbate 20 or 80, SDS may be included at a concentration of from about 0.001% to 2%, preferably 0.01% to 1%. The claimed fusion protein formulations may also contain preservatives, stabilizers, solvents or cosolvents. Preferred solvents include water for injection, organic solvents such as ethanol, glycerol, and other iso-osmotic solutions.

Various delivery systems are known and can be used to administer the claimed FP3' formulations, for example, as a protein in solution, encapsulation in liposomes, microparticles, microcapsules, by way of recombinant cells or vectors capable of expressing the compound, receptor-mediated endocytosis, etc. Methods of introduction can be enteral or parenteral and include but are not limited to intraocular, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

When treating ocular conditions, an FP3' fusion protein composition may be administered locally to the area in need of treatment.

In some embodiments, an FP3' fusion protein composition is provided as a liquid in solution, suspension, or both, e.g., in the form of eye drops. A drop is considered to contain about 25 microliters of liquid. A liquid composition as referred to herein also includes a gel. The liquid composition may be aqueous or in the form of an ointment and may contain one or more polymers as suspending agents. The FP3' fusion protein composition may also be provided in the form of a solid that can be inserted in the eye, such as for example between the eye and eyelid or in the conjunctival sac. In such case, the solid is generally composed of bioerodible or nonbioerodible polymers.

The an FP3' fusion protein composition typically comprises a therapeutically effective amount of one or more fusion proteins, and a pharmaceutically acceptable carrier. The term "pharmaceutically acceptable" means approved by a government regulatory agency or listed in the U.S. Pharmacopeia or other generally recognized pharmacopeia, e.g., as described in "Remington's Pharmaceutical Sciences". The term "carrier" refers to a diluent, adjuvant, excipient, or vehicle with which the therapeutic is administered. The carriers can be sterile liquids, such as water and oils, including those of petroleum, animal, vegetable or synthetic origin, such as peanut oil, soybean oil, mineral oil, sesame oil and the like. Pharmaceutical excipients generally include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol, etc. An FP3' fusion protein composition may also contain wetting agents, emulsifying agents, or pH buffering agents and may be provide as a solution, a suspension, an emulsion, a tablet, a capsule, a powder, or a sustained-release formulation.

An FP3' fusion protein may be formulated as the neutral or salt form. Aqueous compositions of FP3' fusion protein for administration to the eye have ophthalmically compatible pH and osmolality. In ophthalmic embodiments, pH adjusting agents and/or buffering agents may be an acid such as acetic, boric, citric, lactic, phosphoric or hydrochloric acid; a base such as sodium hydroxide, sodium phosphate, sodium borate, sodium citrate, sodium acetate, or sodium lactate; or a buffer, such as citrate/dextrose, sodium bicarbonate or ammonium chloride. The acid, base, and/or buffer is included in an amount required to maintain pH of the composition in an ophthalmically acceptable range and certain salts can be included to ensure that the osmolality of the composition is in an ophthalmically acceptable range. Salts having sodium, potassium or ammonium cations and chloride, citrate, ascorbate, borate, phosphate, bicarbonate, sulfate, thiosulfate or bisulfite anions may be used for this purpose.

The amount of the fusion protein that will be effective for its intended therapeutic use is determined by standard clinical techniques based on the information provided herein.

The amount of compound administered will, of course, be dependent on the subject being treated, including the subject's weight and age and the nature of the condition, the manner of administration. The FP3' fusion protein may be administered a single time or one or more follow-up doses may be administered such as provided in the expels disclosed herein below. FP3' fusion protein therapy may be provided alone or in combination with one or more other drugs.

In general, the concentration of fusion protein in formulations for clinical use is from 0.01 mg/mL to 1000 mg/mL, with the specific dosage dependent upon the form of the formulation, clinical needs, etc. In general, a daily treatment by intravitreal injection comprises administration of from about 0.01 mg to 100 mg, about 0.1 mg to about 10 mg, or about 0.5 mg to about 5 mg, e.g., 0.2 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 60 mg, 70 mg, 80 mg, 90 mg or 100 mg.

In general, a daily treatment by intravenous injection comprises administration of from about 0.1 to about 50 mg/kg, with the specific dosage dependent upon the form of the formulation, clinical needs, etc. In general, a daily treatment by intravitreal injection comprises administration of from about 0.1 to about 50 mg/kg, 0.5 to about 20 mg/kg or about 1 to about 10 mg/kg, e.g., 0.2 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg or 50 mg/kg.

In general, a daily treatment by eye drop administration comprises administration of from about 0.1 mg to about 50 mg per drop, about 0.5 mg to about 20 mg/drop, or about 1 mg to about 10 mg/drop, e.g., 0.2 mg/drop, 0.5 mg/drop, 1 mg/drop, 2 mg/drop, 3 mg/drop, 4 mg/drop, 5 mg/drop, 6 mg/drop, 7 mg/drop, 8 mg/drop, 9 mg/drop, 10 mg/drop, 11 mg/drop, 12 mg/drop, 13 mg/drop, 14 mg/drop, 15 mg/drop, 16 mg/drop, 17 mg/drop, 18 mg/drop, 19 mg/drop, 20 mg/drop, 21 mg/drop, 22 mg/drop, 23 mg/drop, 24 mg/drop, 25 mg/drop, 26 mg/drop, 27 mg/drop, 28 mg/drop, 29 mg/drop, 30 mg/drop, 31 mg/drop, 32 mg/drop, 33 mg/drop, 34 mg/drop, 35 mg/drop, 36 mg/drop, 37 mg/drop, 38 mg/drop, 39 mg/drop, 40 mg/drop, 41 mg/drop, 42 mg/drop, 43 mg/drop, 44 mg/drop, 45 mg/drop, 46 mg/drop, 47 mg/drop, 48 mg/drop, 49 mg/drop or 50 mg/drop.

In certain embodiments, the FP3' formulations comprise a fusion protein concentration of least about 1 mg/mL, at least about 2 mg/mL, at least about 3 mg/mL, at least about 4 mg/mL, at least about 5 mg/mL, at least about 6 mg/mL, at least about 7 mg/mL, at least about 8 mg/mL, at least about 9 mg/mL, at least about 10 mg/mL, at least about 15 mg/mL, or at least about 20 mg/mL.

The pH of the claimed formulations is typically from about pH 5.0 to about pH 9.0, from about pH 7.0 to about pH 8.7, from about pH 7.5 to about pH 8.3, or about pH 7.9.

In certain embodiments, the claimed formulations comprise a citrate buffering agent which is at a concentration of from about 1 mM to about 100 mM, from about 5 mM to 75 mM, from about 10 mM to 55 mM, or about 10 mM.

In certain embodiments, the claimed formulations comprise a carbohydrate excipient such as sucrose, at a concentration of from about 1% to about 20%, about 5% to 15%, or about 8%.

In certain embodiments, the claimed formulations comprise a cationic amino acid such as arginine, at a concentration of from about 1 mM to about 400 mM, about 50 mM to 200 mM, or about 100 mM.

In certain embodiments, the claimed formulations comprise a polysorbate 20 at a concentration of from about 0.001% to about 1%, about 0.001% to about 0.1%, about 0.01% to about 0.1%. or about 0.05%.

Combination Therapy

An FP3' fusion proteins may be administered in combination with one or more additional compounds or therapies. The combination therapy may be administered in a single formulation which includes an FP3' fusion protein and one or more additional agents, or a formulation which includes an FP3' fusion protein and one or more additional agent(s) in a separate formulation. In the latter case, the FP3' fusion protein and the one or more additional agents may be administered using a different treatment regimen. For example, the FP3' fusion protein and one or more additional agents may be administered concurrently, or sequentially.

Kits

Kits comprising packaging material and an FP3' fusion protein are provided herein, where the packaging material comprises a label or package insert which indicates the use of the FP3' fusion protein for treatment of angiogenesis-related eye disease or for tumor regression.

In Vitro Evaluation of the Biological Activity of FP3' Fusion Protein

The quality of the fusion protein was assayed by validated methods, including but not limited to Edman degradation, molecular weight determination (e.g., by SDS-PAGE) and isoelectric point determination. Size exclusion chromatography (SEC) and HPLC using UV detection was applied to assay the purity of product.

An in vitro VEGF binding assay (Example 5); endothelial cell proliferation assay (Example 6); chemotactic migration assay (Example 7); endothelial cell capillary formation assay (Example 8); and ex vivo aortic ring sprouting assay (Example 9), were used to show that the purified FP3' fusion protein had a high affinity for VEGF and was biologically active.

In Vivo Evaluation of the Biological Activity of FP3' Fusion Protein Studies in Rhesus Monkeys An in vivo study was carried out in an experimental model of choroidal neovascularization (CNV) induced by perimacular laser treatment in the eyes of rhesus monkeys. The results show that a single intravitreal injection of 300 or 500 μg FP3' effectively inhibited leakage and growth of choroidal neovascularization in rhesus monkeys without evidence of toxicity, as further detailed in Example 12.

Human Clinical Trial

A phase I clinical trial was conducted in men and women over 45 years of age, with choroidal neovascularization (CNV) due to neovascular AMD. The purpose of the study was to determine the safety, maximum tolerated dose (MTD), the proper dose used in the clinic in Phase 2 trials and bioactivity of intravitreal injection of FP3' in patients with neovascular age-related macular degeneration (AMD). The study protocol and results are detailed in Example 13.

The results of the study showed that FP3' has clinical efficacy in increasing best-corrected visual acuity, and in treating edema and hemorrhage in the retina macular region.

Uses of FP3' Chimeric Fusion Protein.

FP3' finds utility in the inhibition of neovascularization with soluble chimeric proteins comprising VEGF FLT-1 and KDR domains. As such, the claimed soluble chimeric fusion proteins find utility in treatment of neovascularization related diseases. Neovascularization occurs when vascular endothelial cells proliferate upon stimulation by physiologically active substances, or mechanical damage.

Growth factors that have been associated directly or indirectly with proliferation of vascular endothelial cells include basic fibroblast growth factor (bFGF), acidic fibroblast growth factor (aFGF), vascular endothelial cell growth factor (VEGF), platelet-derived endothelial cell growth factor (PD-ECGF), tumor necrosis factor-.alpha. (TNF-.alpha.), platelet-derived growth factor (PDGF), epidermal growth factor (EGF), transforming growth factor-alpha. (TGF-alpha.), and hepatocyte growth factor (HGF). Vascular endothelial cell growth factor (VEGF) can be distinguished from the other growth factors by the fact that its action is very specific to vascular endothelial cells. In other words, the VEGF receptor is found in very few cells other than vascular endothelial cells and VEGF secreted by tumor cells is believed to play a major role in neoplastic neovascularization.

In humans there are two known VEGF receptors, FLT and KDR. Since the extracellular domain of the VEGF receptor specifically binds to VEGF with high affinity, and thereby inhibits VEGF activity, it is useful as an inhibitor against neovascularization.

Medical Conditions Related to Neovascularization

It is known that pathological neovascularization can be a symptom or the cause of certain diseases. Examples of pathological neovascularization include the occurrence of a solid tumor, age-related macular degeneration, diabetic retinopathy (accompanied by pathological neovascularization of the retina, which may lead to the loss of eyesight), rheumatoid arthritis, psoriasis, hemangioma, scleroderma, and neovascular glaucomas.

AMD involves a loss of central vision as a result of a progressive degeneration of retinal and underlying tissues in people over the age of 50 years. AMD accounts for about 50% of all cases of registered blindness in the western world. AMD is the main cause of irreversible blindness in the United States and Europe, and the prevalence appears to be increasing. Increasing rates are also being documented in Asia (Koh, A. H. C., et al., Ann. Acad. Med. 31:399-404, 2002). AMD is a devastating disease that destroys central vision in the affected individuals, robbing them of their ability to perform activities necessary for everyday life such as reading and driving (Bressler et al., 1988; Evans, 2001; Gottlieb, 2002). The incidence of significant vision loss associated with AMD is about 2% for those at age 70, and 6% for those at age 80. (Hawkins, B. S., et al., Mol. Vis. 5:26, 1999; Vingerling, J. R., et al. Epidemiol. Rev. 17:347-360, 1995.) In one study, the prevalence of AMD in persons 75 or older has been reported to be 7.8% (Klein et al., 1992). In addition, the total number of people with AMD is expected to triple by the year 2030. (Vinding, T., Acta Opthalmologica 73 (Suppl): 1-32, 1995.)

Methods currently used for treatment of AMD have achieved only limited efficacy, and are ineffective if not started at a relatively early stage of the disease. Thus, there is a critical need in the art for methods of detecting AMD at a stage early enough for effective therapeutic treatment, to prevent loss of vision, and ultimately to prevent development of the disease.

AMD is a slow, progressive disease that involves cells of the outer retinal layers and is characterized by the breakdown of the macula, a small portion of the central retina (about 2 mm in diameter) responsible for high-acuity vision.

Late-onset macular degeneration (i.e., AMD) is generally defined as either "dry" or "wet." The wet ("exudative") neovascular form of AMD affects approximately 10% of those with the disease, and is characterized by abnormal blood vessels, typically resulting in hemorrhage, exudation, scarring, and/or serous retinal detachment. Approximately 90% of patients with AMD have the non-neovascular dry form, characterized by atrophy of the retinal pigment epithelium (RPE) and loss of macular photoreceptor cells. Choroidal neovascularization (CNV) is responsible for progressive loss of central visual acuity in 90% of neovascular/exudative (wet) AMD patients.

There is presently no cure for AMD. Several types of treatments are available, with laser photocoagulation of abnormal vessels in the wet form of the disease being the standard (Gottlieb, 2002; Algvere and Seregard, 2002). This treatment is limited by the fact that only well-delineated neovascular lesions can be treated in this way and that 50% of patients will suffer recurrence of the leakage from the vessels (Fine et al., 2000). Because of the energy of the laser required for this treatment, the photoreceptors in the treated area will also die, and the patient will also often suffer central blindness immediately after the treatment. New neovascular lesions will eventually develop, requiring repeated treatments.

Neovascular age-related macular degeneration has become an increasing problem as the proportion of the population ages. Age-related macular degeneration (AMD) is the leading cause of irreversible blindness among people who are 50 years of age or older in the developed world.

Dry AMD, the most common type, occurs when light-sensitive cells in the macula degrade and central vision begins to slowly fade. Dry AMD has three stages: (1) early AMD, where the presence of drusens, yellow deposits under the retina are evident, but typically there is no vision loss; (2) intermediate AMD, where there are many medium or large-sized drusens evident and blurry areas may be present such that it is more difficult to do regular task; and (3) advanced dry AMD, where light-sensitive cells begin to degrade dramatically and a blurred spot may appear in the central vision. Atrophy may also be evident in advanced stages. Dry AMD can evolve into Wet AMD.

Wet AMD is more severe and vision loss occurs more rapidly. In wet AMD, small, abnormal new blood vessels form which are very thin and fragile and will break and leak. The blood and fluid eventually causes damage to the macula and causes rapid loss in vision. Wet AMD is the leading cause of blindness for people over the age of 65 in the US and Europe.

Diabetic Retinopathy (DR) can lead to significant vision impairment and is a major complication of diabetes, which over 20 million Americans. Diabetic Macular Edema (DME) is a common complication of DR that involves fluid collection in the macula. DME is the most prevalent cause of moderate visual loss in patients with diabetes.

Combined, AMD and DR are the two of the leading causes of adult blindness in the developed world. In both conditions, severe visual loss is caused by a combination of fluid build-up around the retina and the unnatural growth of blood vessels in the back of the eye.

Conventional laser photocoagulation and photodynamic therapy (PDT) are the most common therapeutic modalities for CNV, however, visual outcome is poor after the treatment of most patients. Verteporfin PDT (Visudyne; Novartis, East Hanover, N.J.) has been shown to stabilize or slow down vision loss in patients with neovascular AMD but requires repeated treatments which may be associated with cumulative damage to normal retinal structures. Neither of these options are effective for all patients with neovascular AMD, and improved or even stabilized visual acuity (VA) is not commonly achieved even with treatment.

Recent research has shown that vascular endothelial growth factor (VEGF) is responsible for many ocular pathologies involving neovascularization. Over the past several years several new agents targeting VEGF have become commercially available for intraocular use. Ongoing trials of anti-VEGF therapies have shown efficacy in treating age related macular degeneration with many patients experiencing improvement in vision. However, there remains a need for development of additional and improved products for treatment of age related macular degeneration and other blinding diseases. Further developments interacting with various steps in the angiogenic cascade are under clinical or preclinical evaluation.

Recently, the therapies that aimed at VEGF-A as the target for the management of CNV associated with AMD. Currently, two inhibitors of VEGF, pegaptanib (MACUGEN®; Eyetech; Pfizer; anti-VEGF 165 aptamer; a sterile, aqueous solution containing pegaptanib sodium for intravitreal injection) and ranibizumab (Lucentis; an antibody fragment which binds to VEGF-A), are approved by the FDA for the treatment of advanced or wet AMD. Both drugs inhibit ocular neovascularization efficiently, however, frequent administration was required to maintain a therapeutic effect on VEGF inhibition. This requires patients to receive an intravitreal injection every four to six weeks.

Lucentis was approved by the U.S. Food and Drug Administration (FDA) in June of 2006 for the treatment of advanced, or wet, AMD. The approval was based on evidence from clinical trials showing that Lucentis slows the rate of progression of vision loss from wet AMD. In addition to a low rate of developing vision loss, approximately one-third of patients treated in these trials had some improvement in vision, as measured on an eye chart, at 12 months. See, e.g., New Engl. J. Med. 355:1419, 2006 and New Engl. J. Med. 355:14321, 2006.

A third drug, Avastin (bevacizumab) is closely related to Lucentis. It was approved by the FDA in 2004 as an intravenous treatment for patients with advanced colorectal cancer and has been available for "off-label use" for other health conditions. It has been widely used off-label to treat wet AMD. Avastin is thought to remain in the eye longer than Lucentis and therefore possibly allow for less frequent injections. The FDA is concerned about the off-label use because the half-life of Avastin is about 100 times slower than Lucentis and manufacturing standards differ for cancer and ophthalmic drugs. Particulate matter must be very low in drugs used in the eye, and Avastin is not manufactured with that in mind.

Lucentis binds more strongly to VEGF protein than Avastin, a full-length antibody, that can also cause inflammation. The antibody fragments in Lucentis are 1/3 the size of Avastin antibodies, so they are capable of better penetration through the retinal layers. However, the need for frequent administration remains an issue.

These limitations provide an opportunity to develop better VEGF inhibitors that can potentially be administered less frequently and act more potently.

"VEGF-TRAP eye" is a fusion protein that binds all forms of Vascular Endothelial Growth Factor-A (VEGF-A) and Placental Growth Factor (PLGF). Both VEGF-A and PLGF are proteins that are involved in the abnormal growth of new blood vessels. Interim results of clinical trials show that the VEGF-TRAP eye may be efficacious in treating angiogenesis-related eye diseases. However, VEGF-TRAP does not bind VEGF in vitro as well as FP3' ($IC_{50}$ for FP3' is 10 pM and $IC_{50}$ for VEGF-TRAP is 30 pM); has a lower association constant and a higher dissociation constant for VEGF than FP3'. FP3' has a theoretical pI of 8.48, and an actual (measured) pI of 6.2-7.0). In contrast, VEGF-TRAP has a theoretical pI of 8.58, and an actual (measured) pI of 8.82. In addition, the results of Phase 2 clinical studies and the Phase 3 clinical trial design for use of VEGF-TRAP in treatment of AMD suggest that it will need to be administered more frequently in patients than FP3'. A Phase 2, 5 arm clinical trial was carried out including a total of 159 patients where in two arms each patient received VEGF TRAP treatment every 4 weeks, and in 3 arms each patient received VEGF TRAP treatment every 12 weeks. At 12 weeks, the mean gain in visual acuity was 5.7 letters. In general, those patients receiving the treatment every 4 weeks did better than those patients receiving the treatment every 12 weeks. (Heier J., Program and abstracts of the 40th Annual Scientific Meeting of the Retina Society; Sep. 27-30, 2007; Boston, Mass.). In contrast, for FP3', a single injection has demonstrated efficacy for at least 7 months. In comparison to VEGF-TRAP, FP3' has (1) a higher binding affinity to VEGF; (2) a longer half life (likely due to it's lower charge leading to a longer circulation time in the; (3) a relatively greater association rate to VEGF and a lower disassociation rate to VEGF; and (4) the inclusion of KDR domain 4 which helps increase the dimerization of the fusion protein.

The claimed FP3' fusion protein may be administered by intravitreal or intravenous injection or using eye drops to treat various angiogenesis-related eye diseases including age-related macular degeneration (AMD), diabetic retinopathy, choroidal neovascularization (CNV), cystoid macular edema, diabetic macular edema, retinal vascular occlusion, corneal neovascularization, corneal transplantation, neovascular glaucoma, pterygium, chronic conjunctivitis, angiogenesis related therapy failure such as laser coagulation, and surgical retinal transplantation.

Corneal neovascularization is the excessive in growth of blood vessels from the limbal vascular plexus into the cornea, caused by a low reception of oxygen, which is generally not received from the bloodstream, but through the air. One of the most common causes is contact lens wear, and to a greater extent, continued use of extended wear contacts. The condition could threaten one's eyesight in the elevated stages Treatment with the FP3' fusion proteins can also be combined with other therapies such as photosensitizers or laser therapy. Unique to FP3' is the inclusion of extracellular domain 4 of VEGF receptor 2 (KDR). While the mechanism is not part of the invention, the inventors believe domain 4 of KDR provides for improved three-dimensional structure and increased dimerization efficiently, which makes FP3' have a high affinity for VEGF, together with a lower isoelectric point (PI), and a prolonged clearance time for FP3' in the vitreous.

This allows a single intravitreal administration of FP3' to provide a clinical effect for 7 months or longer.

When compared with Avastin, the affinity of FP3' for VEGF is 50 times greater than that of Avastin and equally more efficient in inhibiting the proliferation of human umbilical vein endothelial cells induced by VEGF.

The results presented herein illustrate the surprisingly superior efficacy of FP3' in treating various angiogenesis related eye diseases, as well as clinical formulations of FP3' that have good stability, appear safe, and lack significant side effects, as detailed in the following examples.

All publications mentioned herein are incorporated herein by reference in their entirety for the purpose of describing and disclosing the compositions and methodologies which are described in the publications which might be used in connection with the presently claimed invention. The publications discussed herein are provided solely for their disclosure prior to the filing date of the present application. Nothing herein is to be construed as an admission that the invention is not entitled to antedate such a disclosure by virtue of prior invention.

Although the foregoing has been described in some detail by way of illustration and example for purposes of clarity and understanding, it will be apparent to those skilled in the art that certain changes and modifications may be practiced. Various aspects of the claimed invention have been achieved by a series of experiments, some of which are described by way of the following non-limiting examples. Therefore, the description and examples should not be construed as limiting the scope of the invention, which is delineated by the appended description of exemplary embodiments.

EXAMPLES

Example 1

Clone Selection in CHO DUXB11 Cells

Standard molecular biology techniques were used to insert the FP3' coding sequence into the pCMVi expression vector (unpublished results; Kanghong Biotechnology, Ltd.) at a multiple cloning site downstream of the CMV promoter. CHO DUXB11 cells were transfected with the recombinant pCMVi expression vector using an Amaxa Nucleofector™ II Transfector. The transfected CHO DUXB11 cells were grown in IMEM (SAFC Biosciences) containing 1% HT supplement (Gibco) and 10% FBS (SAFC Biosciences), and colonies were screened and selected from the transfected pools based on recombinant protein expression using a standard immunoassay which captures and detects human Fc. More than 3000 colonies were selected for high recombinant protein expression and amplified in the presence of methotrexate (MTX; Sigma) using a stepwise increase in MTX concentration with subsequent culture steps to select for clones that produced the most recombinant fusion protein. A series of single clones with good growth and high productivity was selected. These high producing clones had a specific productivity of recombinant protein of about 25 pg/cell/day.

The selected clones were cultured in IMDM (SAFC Biosciences) with 10% FBS (SAFC Biosciences), then adapted to suspension by removing FBS gradually or directly to obtain suspension clones. Five clones with good growth and high fusion protein productivity that were shown to have a specific productivity of about 20 pg/cell/day were evaluated for stability. Stability was determined based on the stability of fusion protein expression during long term culture, including volumetric productivity, cell growth, characteristics of the recombinant protein, and stability of the gene of interest. This process was used to characterize and select clone(s) to be used for producer cells. A frozen cell bank of clonal producer cells was created for future use.

Example 2

Expression of Recombinant Fusion Protein in CHO Cells

A frozen vial containing cells of a characterized production clone was taken from a cell bank and cultured in serum free medium (Sigma) containing MTX. Cells were cultured at 37° C. in a 5% CO2 atmosphere using a Form a Scientific incubator and the culture was expanded for about 2 weeks using a sequence of T-flasks (Falcon), and shaker flasks (Bellco) prior to inoculating a 5 L Celligen plus bioreactor (New Brunswick Scientific). Cells were maintained in the exponential growth phase throughout the expansion process. The cells were cultured in suspension for about 5 days in a 5 L bioreactor until the viable cell density reached $2.5 \times 10^6$ cells/ml. Then they were transferred to a 30 L stainless steel bioreactor (New Brunswick Scientific) at a density of $5 \times 10^6$ cells/ml and cultured in fed-batch mode for about 15 days.

In the 30 L bioreactor, the temperature was maintained at 37° C. and dissolved oxygen was controlled at 40% saturation. The pH of the media was maintained at 7.0 by addition of $CO_2$ or sodium carbonate. The suspension culture medium was the same serum free medium (Sigma) as the expansion medium, however, there was no MTX in the medium. Concentrated feed medium was added to the reactor every 2 days, with glucose and glutamine solution supplemented to ensure a glucose and glutamine concentration of not less than 2 g/L and 1 mmol/L, respectively. The maximum viable cell density reached $6.5 \times 10^6$ cells/ml. The final volumetric concentration of the fusion protein was determined to be approximately 900 mg/L as determined by an HPLC-based Protein A assay at the end of culture.

Example 3

Fusion Protein Purification

The fusion protein production culture was harvested from the 30 L stainless steel bioreactor after fed-batch fermentation, clarified by depth filtration or centrifugation, and sterile filtered using a 0.2 um filter.

The fusion protein was initially captured by affinity chromatography using a protein A resin, with high specificity for the Fc portion of the fusion protein. After loading the protein A resin, the protein was washed with a large volume of equilibrating buffer to remove any unbound contaminating protein. The fusion protein was eluted from the resin with a pH 3.5 buffer. The fusion protein fractions were pooled, followed by a validated low pH virus inactivation process.

After low pH incubation, the captured fusion protein pool was further purified by cation exchange chromatography to remove the majority of impurities. An isocratic or gradient concentration of sodium chloride was used to elute the protein of interest. The fraction corresponding to the fusion protein was pooled for the next purification step.

Several methods were employed in the polishing process in order to remove particular impurities, such as leached protein A, protein dimers and aggregates, host cell proteins (HCP), host nucleic acids, and virus. The multimodal medium, Capto™ adhere, worked well, however, traditional size exclusion chromatography (SEC) also gave a good result. A Mustang Q membrane (Pall Biopharmaceuticals) provided a very effective and specific binding affinity for nucleic acids and viruses, and was applied to reduce these impurities within the fusion protein pool in a flow-through mode.

In order to completely remove any contaminating viruses in the purified fusion protein, the pools from the polishing step were passed through a nanofilter with nominal pore size of 20 nm using a validated virus inactivation process. Finally, the fusion protein was concentrated using a tangential flow ultrafiltration (UF) membrane and the buffer was exchanged by diafiltration. The concentrated protein was recovered from the UF system, and sterile filtered using a 0.2 um membrane filter, aliquoted, and kept at 4° C. or frozen for long term storage.

The quality of the fusion protein was assayed by validated methods. Edman degradation analysis showed that fusion protein had the expected N-Terminal sequences. The KDR/Flt-1 and Fc portion of the fusion protein were identified by specific antibodies, respectively. The molecular mass of fusion protein was analyzed by SDS-PAGE. The isoelectric point was also determined. Size exclusion chromatography (SEC) HPLC using UV detection was applied to assay the purity of product, and the results showed that >95.0% of fusion protein was a monomer. The molecular purity was also analyzed by SDS-PAGE, which showed >95.0% of fusion protein had same mobility.

A binding assay showed that the purified fusion protein had a high affinity for VEGF with an IC50≦50.0 pM. Low levels of a higher molecular weight species, mainly dimer, were found in the SEC HPLC assay. Ion exchange chromatography (IEC) HPLC also showed low levels of fragments or other variants. Small amounts of other impurities, such as host cell protein (HCP), nucleic acid, endotoxin, and leached ligand protein A, were also identified and quantified by validated methods.

Example 4A

Stability of a 10 mg/ml Liquid Formulation of the Fusion Protein

A liquid formulation containing 10 mM succinate, 0.05% polysorbate 20, 9% trehalose, and 10 mg/ml fusion protein with a pH of 6.0, was stored at 4° C., and samples were tested at 0, 1, 2, 3, 6, 9, 12 and 24 months. Stability was determined by SEC-HPLC, and activity was determined by ELISA. The results, shown in Table 1, illustrate that the fusion protein was aggregated rapidly when stored at 4° C., however, the affinity of binding to VEGF165 was consistent.

TABLE 1

Stability of a 10 mg/ml Formulation of the Fusion Protein at 4° C.

Stability of 10 mg/ml Fusion Protein Stored at 4° C.

| Months | Protein Content mg/mL | Binding Assay (pM) | % Native Configuration |
|---|---|---|---|
| 0 | 10.0 | 13.6 | 97.6 |
| 1 | 9.4 | 13.0 | 96.6 |
| 2 | 10.2 | 11.0 | 96.9 |
| 3 | 10.2 | 15.8 | 96.9 |
| 6 | 10.0 | 14.8 | 95.0 |
| 9 | 10.4 | 14.8 | 94.6 |
| 12 | 10.0 | 15.9 | 91.6 |
| 24 | 10.0 | 13.1 | 87.9 |

A liquid formulation of the fusion protein containing 10 mM succinate, 0.05% polysorbate 20, 9% trehalose, and 10 mg/ml fusion protein with a pH of 6.0, was stored at −20° C., and samples were tested at 0, 1, 2, 3, 6, 9, 12 and 24 months. Stability was determined by SEC-HPLC, and activity was determined by ELISA. The results, shown in Table 2, illustrate that 97.3% and 97.4% of the fusion protein remained intact at 12 and 24 months, respectively.

TABLE 2

Stability of a 10 mg/ml Formulation of the Fusion Protein at −20° C.

Stability of 10 mg/ml Fusion Protein Stored at −20° C.

| Months | Protein Content mg/mL | Binding Assay pM | % Native Configuration |
|---|---|---|---|
| 0 | 10.0 | 13.6 | 97.6 |
| 1 | 9.8 | 13.9 | 97.1 |
| 2 | 10.5 | 11.5 | 96.8 |
| 3 | 9.9 | 11.3 | 96.3 |
| 6 | 10.6 | 18.6 | 97.5 |
| 9 | 10.3 | 13.9 | 98.4 |
| 12 | 11.0 | 11.2 | 97.3 |
| 24 | 11.0 | 13.7 | 97.4 |

A different liquid formulation, containing 5 mM phosphate, 5 mM citrate, 100 mM NaCl, 0.1% polysorbate 20, 20% sucrose, and 10 mg/ml fusion protein at a pH of 6.0 was tested for stability and activity over 24 months when stored at 4° C. The results are shown in Table 3. Stability was determined by SEC-HPLC, and activity was determined by ELISA. The results, shown in Table 3, illustrate that 98.5% and 96.3% of the fusion protein remained intact at 12 and 24 months, respectively.

TABLE 3

Stability of a 10 mg/ml Formulation of the Fusion Protein at 4° C.

Stability of 10 mg/ml Fusion Protein Stored at 4° C.

| Months | Protein Content mg/mL | Binding Assay pM | % Native Configuration |
|---|---|---|---|
| 0 | 10.4 | 9.3 | 98.6 |
| 1 | 10.0 | 13.0 | 99.9 |
| 2 | 10.1 | 14.9 | 99.6 |
| 3 | 10.4 | 14.0 | 99.5 |
| 6 | 10.5 | 17.6 | 98.8 |
| 9 | 10.0 | 27.0 | 99.2 |
| 12 | 10.0 | 15.4 | 98.5 |
| 24 | 9.8 | 9.9 | 96.3 |

A liquid formulation containing 5 mM phosphate, 5 mM citrate, 100 mM NaCl, 0.1% polysorbate 20, 20% sucrose, and 10 mg/ml of fusion protein at a pH of 6.0 was tested for stability and activity over 24 months when stored at −20° C. The results are shown in Table 4. Stability was determined by SEC-HPLC, and activity was determined by ELISA. The results, shown in Table 4, illustrate that 98.8% and 98.6% of fusion protein remained intact at 12 and 24 months, respectively.

TABLE 4

Stability of a 10 mg/ml Formulation of the
Fusion Protein at −20° C.

Stability of 10 mg/ml Fusion Protein When Stored at −20° C.

| Months | Protein Content mg/mL | Binding Assay pM | % Native Configuration |
|---|---|---|---|
| 0 | 11.4 | 9.3 | 98.6 |
| 1 | 11.0 | 14.7 | 99.7 |
| 2 | 10.3 | 14.3 | 99.5 |
| 3 | 10.5 | 13.0 | 99.2 |
| 6 | 10.6 | 17.8 | 99.1 |
| 9 | 10.0 | 27.3 | 99.4 |
| 12 | 10.0 | 12.7 | 98.8 |
| 24 | 10.1 | 9.90 | 98.6 |

Example 4B

Stability of a 20 mg/ml Liquid Formulation of the Fusion Protein

A liquid formulation containing 5 mM citrate, 100 mM Arg, 0.05% polysorbate 20, 8% sucrose, and 20 mg/ml of fusion protein at a pH of 7.9 was tested for stability and activity for about 4 months when stored at 4° C. The results are shown in Table 5. Stability was determined by SEC-HPLC, and activity was determined by ELISA.

TABLE 5

Stability of a 20 mg/ml Formulation of the Fusion Protein at 4° C.

Stability of 20 mg/ml Fusion Protein Stored at 4° C.

| Months | Protein Content mg/mL | Binding Assay pM | pH | % Native Configuration |
|---|---|---|---|---|
| 0 | 19.8 | 14.3 | 8.0 | 99.0 |
| 1 | 20.7 | 10.2 | 7.8 | 98.5 |
| 2 | 19.8 | 12.6 | 7.9 | 98.7 |
| 3 | 20.6 | 10.5 | 7.9 | 98.0 |
| 4 | | | | 98.3 |

Example 5

VEGF Binding Assay

Figure 2:
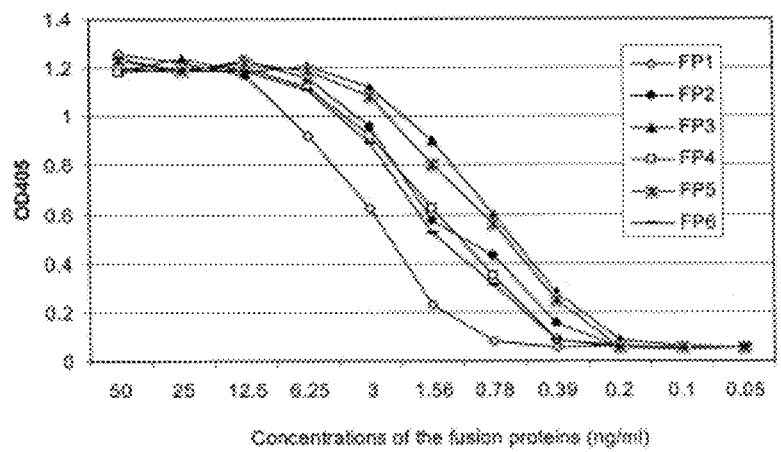
FIG. 2 is a graphic depiction of the results of an assay used to evaluate the binding affinity of FP3', Avastin and VEGF-TRAP for vascular endothelial growth factor (VEGF). The binding assay was used to determine the amount of free VEGF after incubation of human VEGF165 with varying concentrations FP3', Avastin or VEGF-TRAP. The amount of unbound VEGF165 was measured, revealing that the mean $IC_{50}$ for FP3' is 10 pM, the $IC_{50}$ for Avastin is 420 pM and the $IC_{50}$ for VEGF-TRAP is 30 pM.
Figure 3A:
FIG. 3 illustrates the effect of VEGF, as compared to various concentrations of VEGF+FP3' on chemotactic migration (VEGF-mediated migration of endothelial cells), as indicated by the control (FIG. 3A); VEGF (FIG. 3B); VEGF+FP3' (5 μg/600 ml) (FIG. 3C); VEGF+FP3' (10 μg/600 μL) (FIG. 3D); and VEGF+IgG (20 μg/600 μL) (FIG. 3E).
Figure 3B:
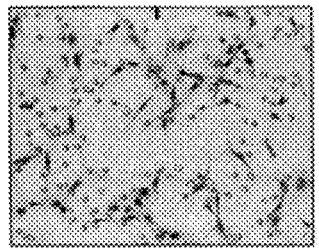
Figure 3C:
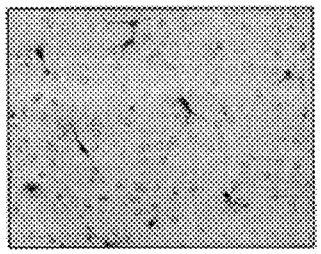
Figure 3D:
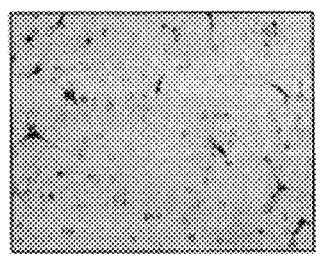
Figure 3E:
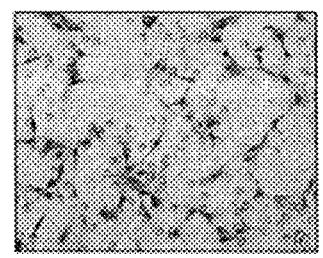

The affinity of the FP3' fusion protein for VEGF was determined by 10 pm of human VEGF to a test tube, followed by addition of FP3', Avastin or VEGF-TRAP in the same volume at different dilutions, followed by mixing and incubation at 37 degrees C. for 1 hour. After 1 hour the amount of the free VEGF in the tube was determined using a VEGF ELISA kit (DY293B; R&D, Minneapolis, Minn.) to detect free human VEGF in mixtures of FP3' (at a concentration range of from 0.1 pM to 0.5 nM) and determination of $IC_{50}$. $IC_{50}$ is the concentration of FP3', Avastin or VEGF-TRAP that corresponds with half (50%) of free VEGF. The results demonstrate that FP3' at 41 nM completely blocked VEGF-induced cell proliferation, and FP3' at 10.7 nM blocked 82.6% of cell proliferation. FIG. 2 shows that the mean $IC_{50}$ for FP3' is 10 pM, the mean $IC_{50}$ for Avastin is 420 pM and the mean $IC_{50}$ for VEGF-TRAP is 30 pM.

Example 6

Endothelial Cell Proliferation Assay

Materials: Cells were Human Umbilical Vein Endothelial Cells (HUVECs), clone Cascade Biologic™; and culture media was M-200, containing penicillin (100 U/ml), streptomycin (100 U/ml) and L-glutamine (2 mM). VEGF was VEGF 121 (R&D) and detection was accomplished with CCK-8 (Dojindo).

HUVECs were seeded at a density of $5 \times 10^4$ cells/well in gelatin-coated 96-well plates and incubated in M-200 medium for 24 hours, followed by incubation with different concentrations of FP3', Avastin or VEGF-TRAP in the presence of 0.2 nM VEGF for 4 days. Proliferation was measured by treatment with the CCK-8 reagent for 2 h at 37° C. Absorbances were read on a microplate reader at 570/630 nm. Cell growth was dramatically inhibited by FP3', Avastin and VEGF-TRAP.

Example 7

Chemotactic Migration Assay

Chemotactic motility of HUVECs in response to FP3' was assessed using a Transwell membrane assay with 6.5-mm diameter polycarbonate filters (8 μm pore size). Various concentration of FP3' (0.5 to about 50 μg/ml) was incubated with the fresh M199 medium (1% FBS) containing 10 ng/ml of VEGF for 30 min at room temperature (RT) before seeding, followed by placement in the lower wells. HUVECs incubated in M199 containing 1% FBS for 6 hrs were harvested after trypsin treatment, and $1 \times 10^5$ cells per transwell were loaded into the upper wells. The chamber was incubated at 37° C. for 4 h, and unmigrated cells on the upper surface of the filter were removed with a cotton swab. The migrated cells on the lower surface of the filter membrane were subsequently fixed with methanol and stained with H&E. Chemotaxis was quantified by counting the migrated cells with an optical microscope (200×). Ten random fields were counted for each assay, and experiments were repeated at least three times. Migration of unstimulated cells served as the control.

FP3' inhibited VEGF-induced migration of HUVECs in a concentration-dependent manner (FIGS. 3A-E). Quantitative analysis showed that 10 μg and 20 μg of FP3' (FIGS. 3D and E) effectively blocked cellular migration by 78.3% and 94.7% ($p < 0.05$ relative to VEGF), respectively. VEGF alone had no significant effect on basal migration of endothelial cells.

Example 8

Endothelial Cell Capillary Formation Assay

Formation of capillary-like structures by HUVEC on a basement membrane matrix preparation was utilized to assess the anti-angiogenic activity of FP3'. Culture plates (16-nm diameter tissue culture wells) were coated with 250 μl of growth factor-reduced Matrigel for 30 min at 37° C. HUVECs were seeded at $1.5 \times 10^5$ cells/well on the Matrigel bed and cultured in media containing 50 μg/ml of control IgG, FP3' or Avastin, in the presence of VEGF (10 ng/ml) for 20 hr. VEGF at 10 ng/ml and control IgG at 50 μg/ml were used as controls. Capillary networks were photographed (40×; 100×), and the area covered by the tube network was quantified by Image-Pro Plus software (Media Cybermetics Inc., Silver Spring, Md.).

Figure 4A:
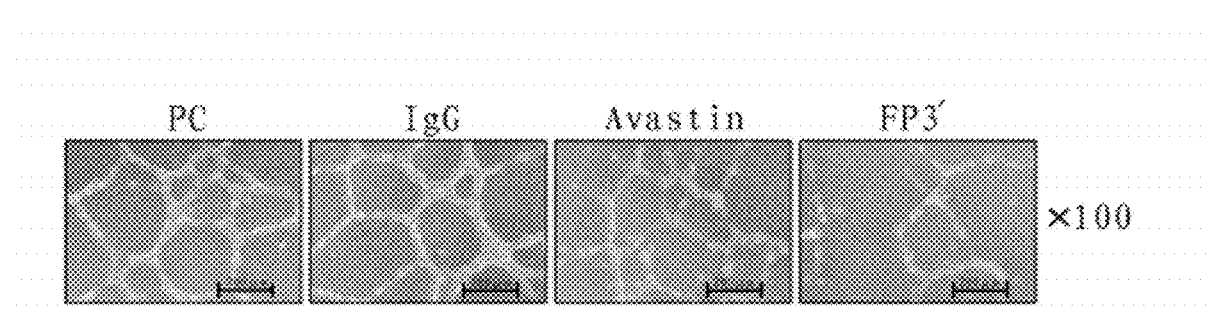
FIGS. 4A and B illustrate the effect of VEGF+IgG, VEGF+Avastin and VEGF+FP3' as compared to a VEGF positive control (+PBS) on endothelial cell capillary formation.
Figure 4B:
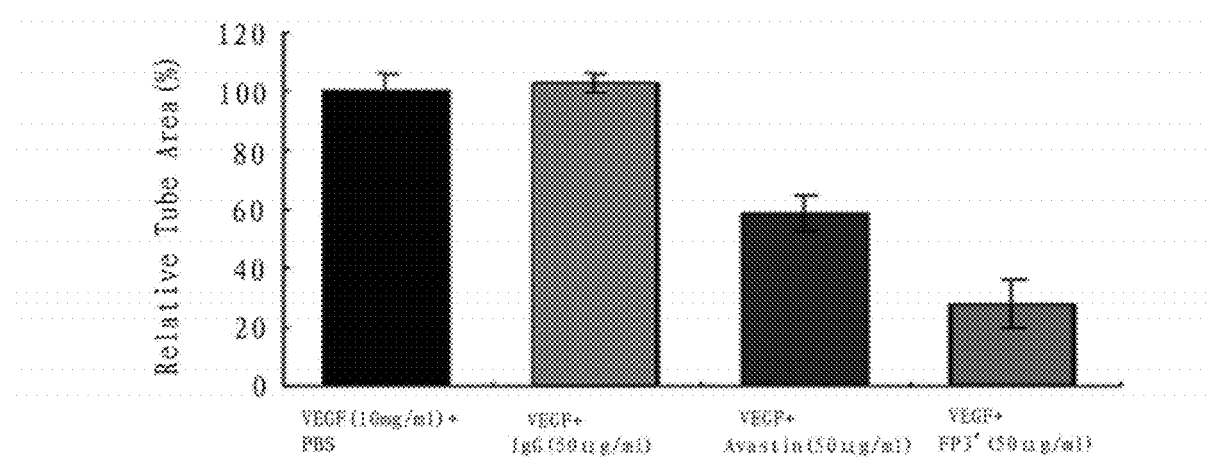

On the Matrigel substratum, stimulation of HUVECs with growth factors like VEGF leads to morphological differentiation of endothelial cells which start to sprout and fuse to form tube-like structures. In the presence of VEGF or control IgG, HUVECs formed organized elongated tube-like structures resembling capillaries with an extensive network. In striking contrast, when FP3' or Avastin was included in the medium, a marked inhibitory effect on the formation of tube-like structures by HUVECs was evident. Based on the vessel counting results, FP3' and Avastin exhibited a 72.3% and 41.3% inhibition of tube formation in relation to the VEGF control, respectively. These findings suggest that FP3' inhibits the tube formation step in angiogenesis (FIGS. 4A and B).

Example 9

Ex Vivo Aortic Ring Sprouting Assay

Aortic ring segments (1 mm) prepared from male Sprague Dawley rats were placed in 48-well Matrigel-coated plates. VEGF (40 ng/ml) in combination with (a) Avastin or (b) FP3' (100 μg/ml) was added to the wells in serum-free human endothelial basal medium-2 (EBM-2, Cambrex Bio Science Walkersville, Inc., Walkersville, Md.). As a control, EBM-2 medium containing VEGF alone was assayed. On day 6, cells were fixed and stained with Diff-Quick. Visual counts of microvessel outgrowths from explants cultures (n=6) were carried out under bright-field microscopy. Results were graded semiquantitatively as 0-5, from the least positive (0) to most positive (5) depending on the degree of vessel sprouting observed. Cultures were scored in a double-blinded manner by three independent observers.

Figure 5A:
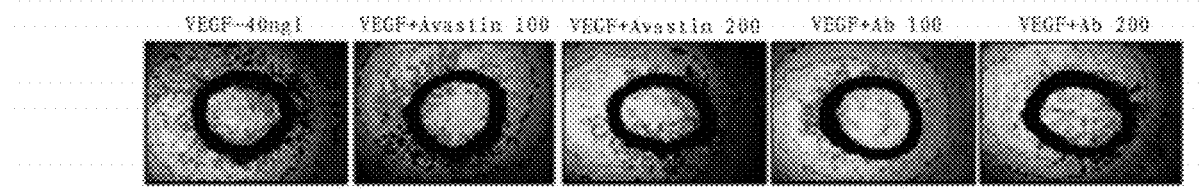
FIGS. 5A and B illustrate the effect of VEGF+Avastin and VEGF+FP3' on ex vivo aortic ring sprouting.
Figure 5B:
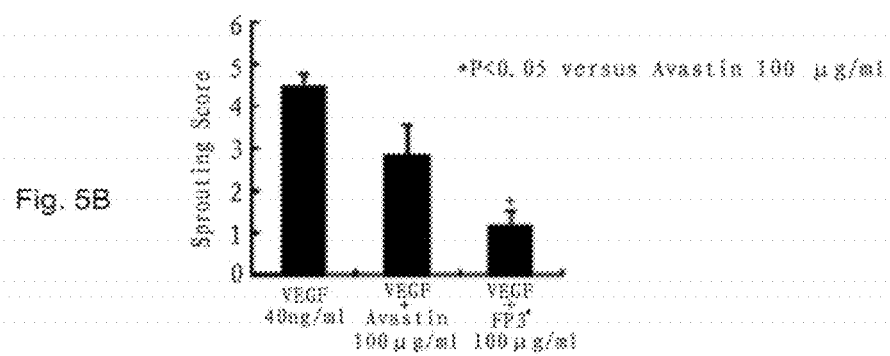
Figure 6:
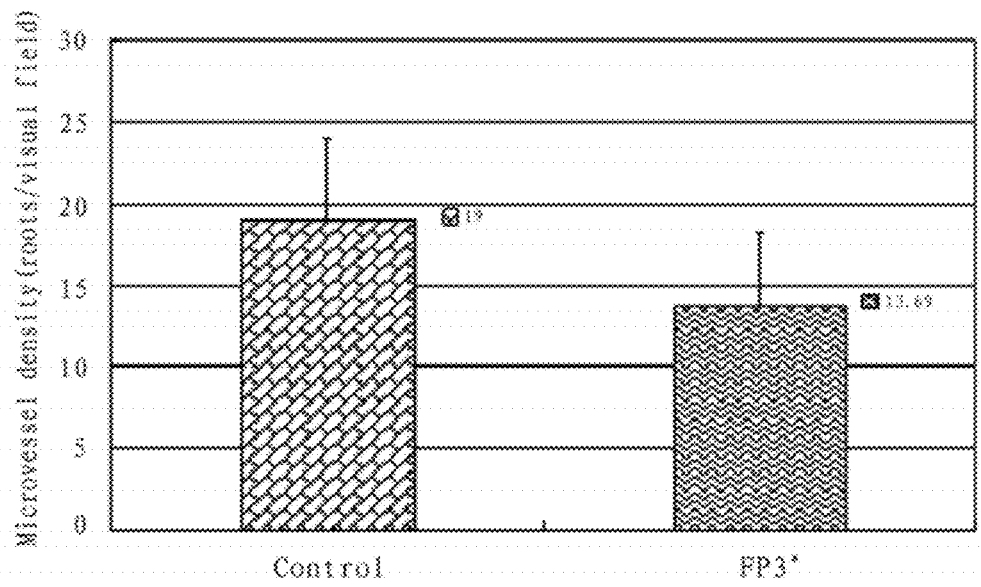
FIG. 6 illustrates the effect of FP3' (+vehicle) on microvessel density (roots/visual field).
Figure 7A:
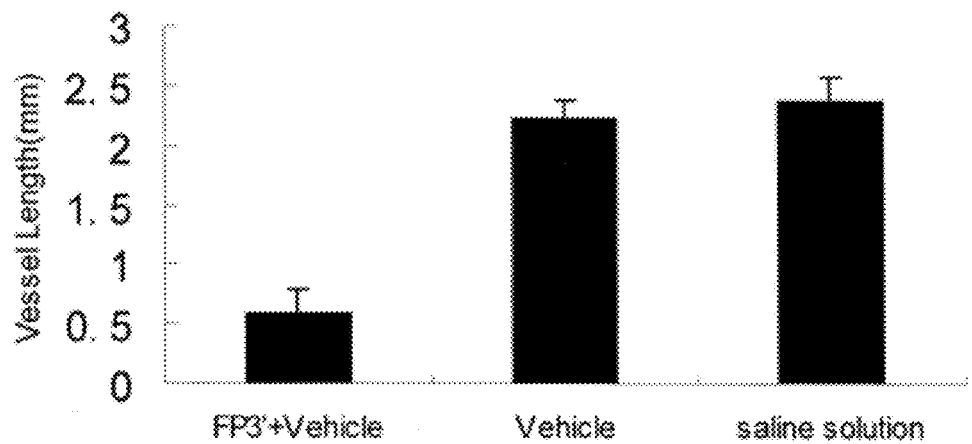
FIG. 7A illustrates the effect of FP3' (+vehicle) eye drops as compared to vehicle and saline solution on vessel length (mm) induced by alkali burn in rats.
Figure 7B:
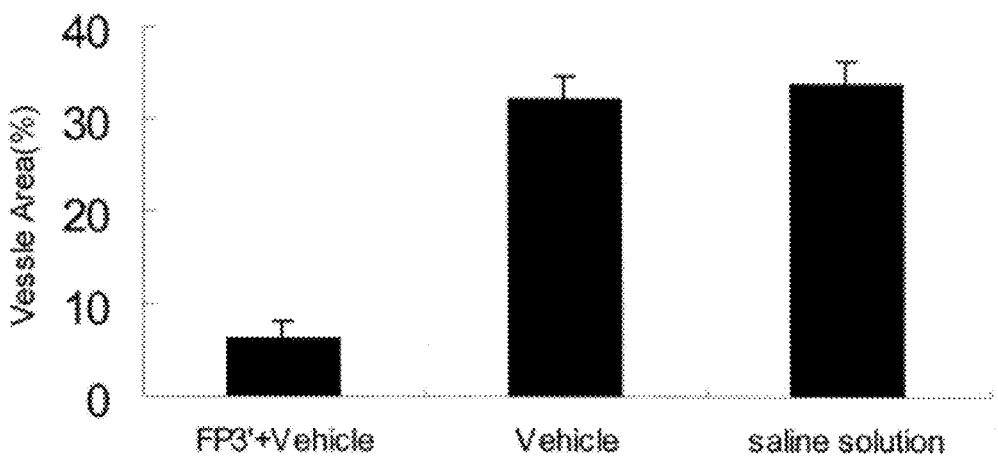
FIG. 7B illustrates the effect of FP3' (+vehicle) eye drops as compared to vehicle and saline solution on vessel area (%) induced by alkali burn in rats.

This system allows for quantitative assessment of effects on microvessel growth, vessel maturation and remodeling, including interactions with periendothelial cells. A strong dose-related inhibition of microvessel growth by both FP3' and Avastin, respectively, was observed, showing a marked delay in the outgrowth of sprouts from the explants, with a regression in both the length and number of vessel sprouts. In a representative experiment, the results of which are shown in FIGS. 5A and B, FP3' demonstrated a 70.4% and 90% inhibition of microvessel sprouting at 100 and 200 μg/ml, respectively, relative to the VEGF control and about 15-33% more inhibition of vessel outgrowth than Avastin, demonstrating the superiority of FP3' to Avastin.

Example 10

Inhibition on Corneal Neovascularization (NV) Induced by Herpes Simplex Virus (HSV) in Mice The slightly scratched right cornea of anesthetized male C57BL6 mice was infected with $5 \times 10^5$ HSV particles. A 10 ul eye drop of FP3' or control solution was administrated twice daily for fourteen days. Corneas were examined for the development of clinical lesions by slit lamp microscopy and stereomicroscopy. The clinical lesion score due to HSV infection was measured in the following manner: 0, normal cornea; 1, mild haze; 2, moderate haze with iris visible; 3, severe haze with iris not visible; 4, severe haze and corneal ulcer; and 5, corneal rupture. The angiogenesis scoring system relied on quantifying the degree of cornea NV formation based on three primary parameters as follows: 1, the circumferential extent of NV (because the angiogenic response is not uniformly circumferential in all cases); 2, the centripetal growth of the longest vessels in each quadrant of the circle; and 3, the length of the longest NV in each quadrant, which was graded between 0 (no NV) and 4 (NV in the corneal center) in increments of about 0.4 mm (with the radius of the cornea equal to about 1.5 mm). According to this system, a grade of 4 for a given quadrant of the circle represents a centripetal growth of 1.2 to 1.5 mm toward the corneal center. The final angiogenesis scores of the four quadrants of the cornea were summed to derive the NV index (range, 0 to 16) for each eye at a given time point.

On Day 14 following HSV infection and initial eye drop treatment, the percentage of animals with a corneal injury score of 2 or less (FIG. 8) and low angiogenesis scores (FIG. 9) were significantly different (p<0.05) between animals treated with FP3' eye drops relative to those treated with vehicle or saline solution. The trend towards increased angiogenesis scores on the cornea induced with HSV was markedly delayed in animals treated with FP3'. The result of this study indicates that FP3' can significantly decrease corneal neovascularization due to HSV-induced injury.

Example 11

Effect of FP3' Eye Drops On Corneal Neovascularization Induced by Suture Placement in Mice Sutures were placed in the peri-central right cornea of C57BL6 mice. Three 10-0 nylon sutures were placed intrastromally with two stromal incursions each extending over 120° of the corneal circumference. The outer point of suture placement was near the limbus, and the inner suture point was near the corneal center equidistant from the limbus. Three days following suture placement, the mice were treated with an eye drop containing 10 mg/ml FP3' fusion protein+vehicle or vehicle alone (control) twice a day for fourteen days. Fourteen days after placement of the 3 interrupted 10-0 sutures into the corneal stroma, mice corneas were excised and examined, and hemangiogenesis (vascular area %) and lymphangiogenesis (lymphatic area %) were evaluated using immunohistochemistry of the corneas with CD31 as the panendothelial and LYVE-1 as the lymphatic endothelial marker. As shown in FIGS. 10A and B, topical administration of FP3' significantly reduced the percentage of both neovascularization and lymphangiogenesis in corneas injured by suture placement.

Example 12

Treatment of Laser-Induced Choroidal Neovascularization (CNV) in the Rhesus Monkeys with FP3'

Experimental CNV was induced by perimacular laser injury to the eyes of 8 rhesus monkeys and confirmed by a comparison before and after the laser treatment at 20, 34, and 48 days, with fluorescence fundus angiography (FFA) and optical coherence tomography (OCT). Rhesus monkeys weighing between 2 and 5 kg, and ranging from 3 to 6 years were anesthetized with 2.5% soluble pentobarbitone (1 ml/kg). Supplemental anesthesia was given with 2.5% soluble pentobarbitone (0.8 ml/kg). Topical ocular anesthesia with proparacaine was also used.

CNV was induced by a laser (Vissulus 532s Laser Photocoagulator, Carl Zeiss Meditec AG, Jena, Germany). Laser photocoagulations were conducted to the perimacular region of monkey eyes. Lesions were placed in the macula with eight spots. Laser lesions were placed in a circular fashion around the macula about one disk diameter from the foveal center.

Care was taken to avoid damaging the fovea with the laser. The approximate laser parameters were as following: spot size, 50 μm; laser power, 300-500 mW; and exposure time, 0.05 seconds, as described in Zhang et al., Mol. Vis. 2008 Jan. 10; 14:37-49.

Twenty days after the laser burn, the monkeys were divided into two groups, the FP3' treatment groups (which were treated with a single administration of 100 μg, 300 μg or 500 μg of FP3') and the control group (which was treated with a single administration of vehicle alone).

General opthalmologic examinations were performed before infliction of laser injury and at regular intervals throughout the study period. The fundus, anterior segment, and intraocular pressure (IOP) were examined by indirect opthalmoscopy, slit-lamp microscopy, and Tono-Pen tonometer in both eyes.

Multifocal electroretinograms (mf-ERGs), color photography and fluorescein fundus angiography (FFA) was carried out before laser treatment and 20 days after the infliction of laser injury. The same procedures were done on days 14 and 28, as also detailed in Zhang et al., Mol. Vis. 2008.

Color fundus photography and fluorescein angiography were used to detect and measure the extent and evidence of leakage of CNV. Angiographically, the burn is hypofluorescent early. If CNV is present, hyperfluorescence develops around the burn, which progresses to late diffuse leakage with dye pooling in the serous detachment surrounding the burn area. The basis for this determination was based on the degree of the leakage on a standardized scale of 1-4, as indicated below in Table 6, which reflects the proportion of grade 4 spots after laser induction of lesions, and following intravitreal injection of FP3'. CNV spots were graded on a scale of 1-4, 20 days after the infliction of laser injury, and on days 14 and 28 after intravitreal injection. The bigger area of grade 4 spots represented greater CNV leakage. The area of neovascularization was significantly less on days 14 and 28, than on day 20 after laser induction in monkey eyes treated with 300 μg or 500 μg of FP3'. In addition, the area was significant lower in the 300 μg and 500 μg FP3'-treated eyes than in the control and 100 μg FP3'-treated eyes (ANOVA, $p<0.001$). Grading scores were defined as follows: 1, no hyperfluorescence; 2, hyperfluorescence without leakage; 3, early hyperfluorescence and late mild leakage; 4, early hyperfluorescence and late severely dye leakage which transit and beyond the borders of the laser burn lesion. See, also FIG. 11, which illustrates the area of grade 4 CNV spots after laser induction of lesions and following intravitreal injection of FP3'

TABLE 6

Proportion Of Grade 4 Spots After Laser Induction Of Lesions And Following Intravitreal Injection Of FP3'

| Groups | Proportion Of Grade 4 spots Day 20 After Laser | Proportion Of Grade 4 spots Day 14 After Intravitreal Injection | Proportion Of Grade 4 spots Day 28 After Intravitreal Injection |
|---|---|---|---|
| Control | 68.75 ± 44.19 | 62.5 ± 35.36 | 62.5 ± 35.36 |
| FP3'(0.1 mg) | 53.13 ± 25.77 | 12.5 ± 25* | 3.13 ± 6.25 |
| FP3'(0.3 mg) | 53.13 ± 25.77 | 12.5 ± 25* | 3.13 ± 6.25* |
| FP3'(0.5 mg) | 71.88 ± 27.72 | 6.25 ± 12.5* | 3.13 ± 6.25* |

Classic CNV similar to human CNV was evident the majority % of the laser spots. Hypo fluorescence in the early phase and fluorescence leakage in the late phase were detected by the FFA. High reflect light echogenic mass and retina edema were detected by the OCT. The histopathologic examinations indicated proliferated fiber-vasculosa membranes in the laser burnt spots. The pathological changes lasted 48 days until the monkeys were killed.

In the eyes of monkeys in groups treated with 300 μg or 500 μg of FP3, choroidal neovascularization leakage was clearly less than before injection, and no leakage was observed after injection. No high reflect light echogenic mass was detected by OCT. However, leakage and high reflect light echogenic mass was evident in the eyes of the monkeys in the 100 μg FP3' treatment and control groups. The reduction of experimental CNV was greater in eyes treated with 300 μg and 500 μg FP3' than in eyes treated with 100 μg FP3' and the control group eyes. There were fiber-vasculosa membrane proliferation in the 100 μg FP3'-treated eyes and control eyes but not in the 300 μg and 500 μg FP3'-treated eyes under histopathologic observation. The results of mf-ERG demonstrated that there was greater improvement in the 300 μg and 500 μg FP3'-treated eyes than in the 100 μg FP3'-treated eyes and control eyes. The results show that a single intravitreal injection of 300 or 500 μg FP3' effectively inhibited leakage and growth of choroidal neovascularization in rhesus monkeys without evidence of toxicity. See, also Zhang et al., Mol. Vis. 2008 Jan. 10; 14:37-49.

Example 13

Phase 1 Clinical Trial—Treatment of Age-Related Macular Degeneration (AMD) with FP3'

A human clinical trial was conducted with the primary objective of evaluation of the safety of FP3' following a single intravitreal injection in patients with wet AMD; to understand the maximum tolerated doses of FP3' administered via this route and to understand the pharmacokinetics of FP3' following intravitreal injection in human subjects. A secondary endpoint was evaluation of the biological activity of PF3' following a single injection by measurement of visual acuity, retinal thickness and CNV size.

Preparation of the Fusion Protein FP3 in Solution for Eye Application

First prepared formulation buffer (including 5 mmol/L disodium phosphate, 5 mmol/L citric acid, 100 mmol/L sodium chloride, 20% sucrose, and 0.1% polysorbate 20, pH 6.0), then thawed appropriate drug substance of FP3 and diluted it with the formulation buffer to required protein concentration (10 mg/mL), and thereby obtained the pharmaceutical composition was aliquoted into sterile vials (5 mL/20 mL). The vials were covered with sterile butyl rubber stoppers, sealed with aluminum caps, labeled and stored in paper boxes under appropriate temperature.

Human Clinical Study

Men and women over 45 years of age, with choroidal neovascularization (CNV) due to neovascular AMD and active primary or recurrent subfoveal CNV that was secondary to AMD, with a lesion size of ≦12 disc areas and an Early Treatment for Diabetic Retinopathy Study (ETDRS) protocol for Best Corrected Visual Acuity (BCVA) score of ≦20/100 in the study eye, were administered a single intravitreal injection of FP3'.

The patients in this study had advanced neovascular AMD; half were legally blind, and the purpose of the study was to determine the safety, maximum tolerated dose (MTD), the proper dose used in the clinic in Phase 2 trials and bioactivity of intravitreal injection of FP3' in patients with neovascular age-related macular degeneration (AMD).

The study was a single center, open, dose-escalation Phase 1 trial with twenty-eight patients enrolled across the 6 dose levels. The patients were treated with 0.05 mg, 0.15 mg, 0.5 mg, 1.0 mg, 2.0 mg and 3.0 mg of FP3' per eye on day 0, with escalation to the next dose level only after the safety and tolerability was established through post-injection day 14 for the previous dose level. The screening period was 14 days; the treatment observation period was 15 days and the post-injection follow-up period was 28 days.

The results show that the dose of intravitreal injection of FP3' at 3.0 mg is safe and well tolerated (i.e. a maximum tolerated dose was not reached). There were no serious or drug-related systemic adverse events, and ocular adverse events were mild to moderate in severity. The most common ocular adverse events were transient intraocular pressure (IOP) elevation after FP3' injection and injection-site subconjunctival hemorrhage. There were no reports of significant ocular inflammation or endophathalmitis.

The results included the following:

"Best Corrected Visual Acuity" (BCVA) was improved from 20.57±18.13 (baseline) to 40.18±21.65 letters at day 42 following FP3' treatment (i.e., an improvement of more than 19 letters, as shown in FIG. 12 which presents the results as the mean and median change in visual acuity, in terms of letters);

mean foveal retinal thickness was reduced from 336.54±130.45 µM (baseline) to 260.57±81.73 µM (FIG. 13);

mean macular size (volume) was decreased from 7.53±1.69 mm³ (baseline) to 6.97±0.97 mm³ (FIG. 14);

mean CNV size was decreased from 5.07±5.02 mm³ (baseline) to 4.43±4.99 mm³; and mean lesion size was decreased from 7.98±6.67 mm³ (baseline) to 7.53±6.47 mm³.

In summary:

intravitreal injection of up to 3.0 mg of FP3' was well-tolerated;

no patients lost visual acuity during the study;

there was a 19.61 mean letter gained best-corrected visual acuity at week 6 (FIG. 12);

85.7% of patients improved visual acuity and 14.3% remained stable;

57.2% of patients gained greater than or equal to 15 letters (≧3 lines) in visual acuity;

28.6% of patients gained greater than or equal to 30 letters in visual acuity;

effects on retinal thickness were rapid, substantial and prolonged and generally persisted throughout the 6-week reporting period;

an increase in mean BCVA of 19.61 letters in all treated patients at day 42; and all patients remain in the study and continue to be observed.

Six additional AMD patients were added to the clinical study described above to compare the efficacy of FP3' with that of Avastin. Each patient was treated with 1.25 mg of Avastin per eye. The result are shown in FIG. 15 which provides a graphic depiction of the effect of FP3' and Avastin on mean visual acuity in patients with AMD.

Following completion of the "official" treatment observation period and the post-injection follow-up period, patients were observed for up to 7 months and no change in visual acuity was evident.

The results of this study show that FP3' has clinical efficacy in increasing best-corrected visual acuity, and in treating edema and hemorrhage in the retina macular region. After FP3' administration, in particular in the high dose group, CNV leakage in most patients was alleviated, and local closure of CNV was evident in some patients.

Example 14

Further Clinical Trials—Treatment with FP3'

Intravitreal injection of the FP3' fusion protein can be combined with surgery, for example, after retinal transplantation. AMD patients could establish their visual acuity baselines after routine eye examinations, and then receive the fusion proteins by intravitreal injection. After treatment, the patients would be observed and examined in a hospital to record the effects of the fusion protein. Typically, the examinations would take place at days 1, 2, 6, 14, 30 and 90 after treatment. If necessary, patients could be given multiple intravitreal treatments every 2 to 8 weeks. The individual doses could be as high as 5 mg to 10 mg per eye.

The invention claimed is:

1. A method for treating an angiogenesis-related eye disease or condition, comprising:
administering to a subject in need thereof, either locally or intravenously, a VEGF receptor fusion protein comprising the amino acid sequence of SEQ ID NO:8,
wherein one or more symptoms of the angiogenesis-related eye disease or condition is improved following administration.

2. The method according to claim 1, wherein the angiogenesis-related eye disease or condition is selected from the group consisting of age-related macular degeneration (AMD), diabetic retinopathy, choroidal neovascularization (CNV), cystoid macular edema, diabetic macular edema, retinal vascular occlusion, corneal neovascularization, corneal transplantation, neovascular glaucoma, pterygium, chronic conjunctivitis, angiogenesis related therapy failure such as laser coagulation, and surgical retinal transplantation.

3. The method according to claim 2, wherein the angiogenesis-related eye disease or condition is AMD.

4. The method according to claim 2, wherein the angiogenesis-related eye disease or condition is diabetic retinopathy.

5. The method according to claim 2, wherein the one or more improved symptoms of the angiogenesis-related eye disease or condition is selected from the group consisting of a decrease in mean choroidal neovascularization (CNV) leakage, improved mean visual acuity, a reduction in mean foveal retinal thickness, a reduction in mean macular size, and a reduction in mean lesion size.

6. The method according to claim 5, wherein the one or more symptoms of the angiogenesis-related eye disease or condition remains improved for at least 7 months following the administration.

7. The method according to claim 1, wherein the fusion protein is administered by intravitreal injection.

8. The method according to claim 7, wherein the fusion protein is administered by an intravitreal injection comprising an amount of from about 0.01 to about 100 mg or from about 0.1 to about 10 mg.

9. The method according to claim 8, wherein following a single intravitreal injection of the fusion protein, the one or more symptoms of the angiogenesis-related eye disease or condition that is improved is selected from the group consisting of a decrease in mean choroidal neovascularization (CNV) leakage, improved mean visual acuity, a reduction in mean foveal retinal thickness, a reduction in mean macular size, and a reduction in mean lesion size.

10. The method according to claim 9, wherein the one or more symptoms of the angiogenesis-related eye disease or condition remains improved for at least 7 months following the administration.

11. The method according to claim 1, wherein the fusion protein is administered by intravenous injection.

12. The method according to claim 11, wherein the fusion protein is administered by an intravenous injection comprising an amount of of from about 0.1 to about 30 mg/kg or from about 0.5 to about 5 mg.

13. The method according to claim 1, wherein the fusion protein is administered using eye drops.

14. The method according to claim 13, wherein the fusion protein is administered by eye drops comprising an amount of from about 0.1 to about 50 mg per eye drop or from about 0.5 to about 5 mg per eye drop.

15. The method according to claim 1, wherein the fusion protein is provided in a formulation that further comprises one or more pharmaceutically acceptable carriers commonly used for ophthalmological therapeutics.

16. The method according to claim 15, wherein the fusion protein is provided as a solution formulation.

17. The method according to claim 16, wherein a 10 mg/ml solution of the fusion protein is stable for at least 24 months at a temperature of −20° C. or for at least 12 months at a temperature of 4° C.

18. The method according to claim 15, wherein the fusion protein is lyophilized.

* * * * *